(12) United States Patent
Lobsiger et al.

(10) Patent No.: US 12,414,845 B2
(45) Date of Patent: Sep. 16, 2025

(54) GENERATION OF A THREE-DIMENSIONAL DIGITAL MODEL OF A REPLACEMENT TOOTH

(71) Applicant: EXOCAD GMBH, Darmstadt (DE)

(72) Inventors: Janik Lobsiger, Darmstadt (DE); Eduardo Peire, Darmstadt (DE); Maik Gerth, Seeheim-Jugenheim (DE); Daniel Michel Peter, Uster (CH)

(73) Assignee: EXOCAD GMBH, Darmstadt (DE)

( * ) Notice: Subject to any disclaimer, the term of this patent is extended or adjusted under 35 U.S.C. 154(b) by 502 days.

(21) Appl. No.: 17/896,208

(22) Filed: Aug. 26, 2022

(65) Prior Publication Data
US 2024/0065815 A1    Feb. 29, 2024

(51) Int. Cl.
*A61C 9/00* (2006.01)
*A61C 13/34* (2006.01)
*G06T 19/20* (2011.01)

(52) U.S. Cl.
CPC ............ *A61C 9/0053* (2013.01); *A61C 13/34* (2013.01); *G06T 19/20* (2013.01); *G06T 2219/2021* (2013.01)

(58) Field of Classification Search
CPC ... A61C 13/34; A61C 9/0053; A61C 13/0004; G06T 19/20; G06T 2219/2021; G06T 7/10; G06T 7/149; A61L 2/10; A61L 2/18; A61L 2/24; A61L 2202/17; G01N 21/94; G16H 20/40; G16H 30/40; G16H 50/20; G16H 50/50; G16H 50/70

USPC .......................................................... 700/98
See application file for complete search history.

(56) References Cited

U.S. PATENT DOCUMENTS

| | | | |
|---|---|---|---|
| 2021/0153986 A1 | 5/2021 | Wirjadi et al. | |
| 2021/0236249 A1* | 8/2021 | Nikolskiy | A61C 13/0004 |
| 2022/0215531 A1* | 7/2022 | Azernikov | G06T 7/11 |
| 2023/0039130 A1* | 2/2023 | Peng | G06N 3/0464 |
| 2023/0334771 A1* | 10/2023 | Shen | A61C 13/34 |

FOREIGN PATENT DOCUMENTS

| | | | |
|---|---|---|---|
| EP | 3669815 A1 | 6/2020 | |
| WO | WO-2020181972 A1 * | 9/2020 | |

* cited by examiner

*Primary Examiner* — Chun Cao
(74) *Attorney, Agent, or Firm* — Perry + Currier

(57) ABSTRACT

Disclosed herein is a dental method that comprises receiving a selection of a replacement tooth for a subject. The method further comprises receiving one or more three-dimensional digital tooth models descriptive of one or more teeth of the subject. The method further comprises receiving a generated three-dimensional digital model of the replacement tooth in response to inputting the one or more three-dimensional digital tooth models descriptive of one or more teeth of the subject into a tooth model generating neural network. The tooth model generating neural network comprises an encoder portion and a decoder portion. The encoder portion is configured for outputting a collective feature vector descriptive of the one or more digital tooth models. The tooth model generating neural network further comprises at least one fully connected layer configured to output a latent space vector into the decoder portion in response to receiving the collective feature vector.

26 Claims, 10 Drawing Sheets

GENERATION OF A THREE-DIMENSIONAL DIGITAL MODEL OF A REPLACEMENT TOOTH

FIELD OF THE INVENTION

The invention relates to dental technology, in particular to the modeling of replacement teeth.

BACKGROUND AND RELATED ART

Dental restorations, like crowns, are usually prepared to match the existing teeth of a subject. In order to ensure this, a skilled dental technician would sculpt the crown to match the existing teeth as well as ensuring that it fits in the space between the adjacent teeth and matched the antagonist teeth.

SUMMARY

The invention provides for a dental method, a computer program, and a dental system in the independent claims. Embodiments are given in the dependent claims.

It can be challenging to correctly model a replacement tooth for a subject. The shape of the replacement tooth should match the subject's existing teeth. Embodiments may provide for an improved means of producing a generated three-dimensional digital model of a replacement tooth. This may be achieved by using a tooth model generating neural network that receives one or more three-dimensional digital tooth models as input. The one or more three-dimensional digital tooth models received as input are descriptive of one or more teeth of the subject. They may, e.g., result from a scan of the teeth of the subject. Using such three-dimensional digital tooth models descriptive of one or more teeth of the subject as an input may have the advantage that a three-dimensional digital model of the replacement tooth generated by the tooth model generating neural network may match the subject's existing teeth. The tooth model generating neural network comprises an encoder portion and a decoder portion. The encoder portion produces a collective feature vector that is translated by one or more fully connected layers into a latent space vector of the decoder portion. An advantage of this is that features of one or more three-dimensional digital tooth models are combined using the collective feature vector and then translated to the latent space vector.

In one aspect the invention provides for a dental method. The method comprises receiving a selection of a replacement tooth for a subject. The selection of a replacement tooth may comprise providing an identifier or label for the replacement tooth. This could, for example, be by providing a name of the replacement tooth or, for example, by providing a number which identifies the tooth according to a standard tooth numbering. For example, a scan, like an intraoral scan, of a subject's dental arch may comprise a tooth to be replaced, like a partially missing or damaged tooth or a prepared tooth, like a tooth stump, which has been prepared for receiving a dental restoration, like, e.g., crown. The selection of a replacement tooth may comprise identifying the replacement tooth by identifying the tooth to be replaced. For example, the selection of a replacement tooth may comprise identifying the replacement tooth indirectly, e.g., by identifying neighbor teeth and/or an antagonist and/or a contralateral tooth of the replacement tooth, e.g., in a scan of one or both dental arches of the patient. The replacement tooth may for example be a tooth that is missing. In other examples the replacement tooth could be a tooth that has been ground down in preparation for receiving, e.g., a crown or other dental restoration.

The method further comprises receiving one or more three-dimensional digital tooth models descriptive of one or more teeth of the subject. The one or more three-dimensional digital tooth models are individual models. Such an individual model may model just a particular tooth of the subject. For example, each of the one or more three-dimensional digital tooth models only a single tooth. In this step there are one or more three-dimensional digital tooth models that are received and these are used to provide data about specific teeth of the subject. These one or more three-dimensional digital tooth models may, e.g., result from a scan, like, e.g., an intraoral scan, of the subject's teeth and thus provide data about the geometry and/or aesthetics of the subject's teeth. This data may enable a generation of a subject-individualized three-dimensional digital replacement tooth model, which matches the geometry and/or aesthetics of teeth already present within the subject's mouth, like existing natural and/or artificial teeth of the subject.

The method further comprises receiving a generated three-dimensional digital model of the replacement tooth in response to inputting the one or more three-dimensional digital tooth models descriptive of the one or more teeth of the subject into a tooth model generating neural network. The tooth model generating neural network comprises an encoder portion and a decoder portion. The encoder portion is configured for outputting a collective feature vector descriptive of the one or more digital tooth models. The tooth model generating to neural network further comprises at least one fully connected layer that is configured to output a latent space vector in response to receiving the collective feature vector. The decoder portion is configured to output the generated three-dimensional digital model of the replacement tooth in response to receiving the latent space vector. In this embodiment, the one or more three-dimensional digital tooth models are input to the tooth model generating neural network and it outputs the generated three-dimensional digital model of the replacement tooth. This may be beneficial because it may provide for an accurate means of generating a three-dimensional digital model of a replacement tooth that matches a subject's existing teeth well.

The one or more teeth of the subject could comprise one or more natural teeth. All the one or more teeth of the subject could be natural teeth. That is to say, they could be real teeth of the subject. A natural tooth is a tooth that is organic and formed by a natural development for the body, i.e., not fabricated or manufactured. Organic portions of a natural tooth include the crown enamel and dentin, the root cementum and dentin, and the enclosed pulp. The one or more teeth of the subject could comprise one or more artificial teeth. All the one or more teeth of the subject could be artificial teeth. An artificial tooth is a tooth fabricated or manufactured in order to be placed in a subject's mouth. Such an artificial tooth may in particular be used to replace a natural tooth of the subject, which has gone missing or damaged such that a replacement is required.

The collective feature vector is a vector which describes the features of the one or more three-dimensional digital tooth models. The latent space vector, in contrast, is a vector which controls how the tooth model generating neural network generates the three-dimensional digital model. A fully connected layer in a neural network connects all the inputs to every activation unit of the next layer, i.e., every neuron in one layer to every neuron in another layer. The at least one fully connected layer is used as a translation between the two. The use of this at least one fully connected layer as a translation between the collective feature vector and the latent space vector may be beneficial because it may enable the individual portions of the tooth model generating neural network to be trained independently. This may for example result in a higher quality generated three-dimensional digital model as well as reducing the amount of data which is necessary to produce good results.

In one example, the dental method may be for generating a subject-specific, i.e., subject-individualized, three-dimensional digital model for an at least partially missing tooth of a subject.

The tooth model generating neural network may be trained by receiving separate three-dimensional digital models, e.g., in form of tooth meshes from raw scans of subjects with a full set of teeth to construct training data. The full sets of teeth may, e.g., be full sets of teeth of mandibular dental arches, full sets of teeth of maxillary dental arches or full sets of teeth of dentitions, i.e., mandibular and maxillary arches. Training data may be constructed from these full sets of teeth, e.g., in form of tooth meshes, by selecting for each of these full sets one tooth of the respective full set as the replacement tooth and using this tooth selected as the ground truth. Other teeth of the respective full sets can be used as input to the tooth model generating neural network during training.

In another embodiment, the method further comprises selecting the tooth model generating neural network for generating the replacement tooth from a collection of tooth model generating neural networks trained for a specific tooth or trained for a specific tooth type using the selection of the replacement tooth. In this embodiment the tooth model generating neural network is trained specifically to replace a particular tooth or a particular type of tooth. This for example may be beneficial because the tooth model generating neural network is more focused and may produce better results with less training. Thus, the collection of tooth model generating neural networks may comprise different tooth model generating neural networks for generating different teeth or different types of teeth. The tooth model generating neural network to be used for generating the replacement tooth may be selected from the collection based on the specific replacement tooth to be generated and/or based on the specific type of replacement tooth to be generated. In some examples, the selection of the tooth model generating neural network may determine the selection of the one or more three-dimensional digital tooth models to be provided as input for the selected the tooth model generating neural network. For example, when a particular tooth model generating neural network is trained, it may be trained using specific teeth as input. In some cases, this method may comprise selecting the one or more three-dimensional digital tooth models in response to the selection of the tooth model generating neural network.

When the tooth model generating neural network is trained for a specific type of tooth, it may for example be a model which specializes in reproducing molars, pre-molars, canines, incisors, or other types of teeth. The collection of tooth model generating neural networks may thus, e.g., comprise a tooth model generating neural networks trained for reproducing molars, a tooth model generating neural networks trained for reproducing pre-molars, a tooth model generating neural networks trained for reproducing canines, and/or a tooth model generating neural networks trained for reproducing incisors.

When the tooth model generating neural network is trained for a specific tooth, it may be trained for a specific one of the 32 teeth usually comprised by a dentition of an adult human. These 32 teeth comprise 16 maxillary teeth and 16 mandibular teeth. The 16 maxillary teeth comprise two contralaterally arranged maxillary central incisors, two contralaterally arranged maxillary lateral incisors, two contralaterally arranged maxillary canines, two contralaterally arranged maxillary first premolars, two contralaterally arranged maxillary second premolars, two contralaterally arranged maxillary first molars, two contralaterally arranged maxillary second molars, and two contralaterally arranged maxillary third molars. The 16 mandibular teeth comprise two contralaterally arranged mandibular central incisors, two contralaterally arranged mandibular lateral incisors, two contralaterally arranged mandibular canines, two contralaterally arranged mandibular first premolars, two contralaterally arranged mandibular second premolars, two contralaterally arranged mandibular first molars, two contralaterally arranged mandibular second molars, and two contralaterally arranged mandibular third molars. Third molars are commonly referred to as wisdom teeth, which usually emerge at ages 17 to 25. These molars may never erupt into the mouth or never form at all. When they do form, they are often removed. The collection of tooth model generating neural networks may thus, e.g., comprise 32 tooth model generating neural networks, each trained for reproducing one of the 32 usually comprised by a dentition of an adult human. Without the third molars, the collection of tooth model generating neural networks may thus, e.g., comprise 28 tooth model generating neural networks. The collection of tooth model generating neural networks may thus, e.g., comprise 16 tooth model generating neural networks, each trained for reproducing one of the 16 usually comprised by a maxillary dental arch of an adult human. Without the third molars, the collection of tooth model generating neural networks may thus, e.g., comprise 14 tooth model generating neural networks. The collection of tooth model generating neural networks may thus, e.g., comprise 16 tooth model generating neural networks, each trained for reproducing one of the 16 usually comprised by a mandibular dental arch of an adult human. Without the third molars, the collection of tooth model generating neural networks may thus, e.g., comprise 14 tooth model generating neural networks.

In another embodiment, the encoder portion comprises a tooth-specific context encoder neural network for each of the one or more three-dimensional digital tooth models. The tooth-specific context encoder neural network is configured to output a tooth feature vector in response to receiving a three-dimensional digital tooth model of the one or more three-dimensional digital tooth models. The tooth model generating neural network is further configured to form the collective feature vector by concatenating the tooth feature vector of at least some of the tooth-specific context encoder neural network.

In this embodiment there is a specific context encoder neural network that is used for each of the one or more three-dimensional digital tooth models. In other words, there is a three-dimensional digital tooth model that is received for each of these teeth and then each of these teeth models are input into its own specific context encoder neural network, which then outputs a tooth feature vector. The tooth feature vector describes the particular model of the one or more three-dimensional digital tooth models. These are then concatenated and then this concatenation is translated into the latent space vector using the at least one fully connected layer. When a particular number of three-dimensional digital tooth models is used as input for generating the three-dimensional digital model of the replacement tooth, e.g., two models, three models, or more models, the encoder portion may comprise a tooth-specific context encoder neural network for each of these three-dimensional digital tooth models, e.g., two tooth-specific context encoder neural networks, three tooth-specific context encoder neural networks, or more tooth-specific context encoder neural networks. For example, the encoder portion comprises a tooth-specific context encoder neural network for each tooth or each type of tooth comprised by a dentition of an adult human. For example, the encoder portion may comprise more tooth-specific context encoder neural networks than the number of three-dimensional digital tooth models being input, i.e., the one or more three-dimensional digital tooth models. In this case, the encoder portion may, e.g., comprise a tooth-specific context encoder neural network for each tooth or each type of tooth comprised by a dentition of an adult human and the one or more three-dimensional digital tooth models being each input into their own specific context encoder neural networks based on the tooth or type of tooth described by the respective three-dimensional digital tooth model.

This embodiment may be particularly beneficial because this is a highly effective and accurate way of producing the generated three-dimensional digital model of the replacement tooth so that it matches a particular subject, e.g., matching characteristic geometric and/or aesthetic features of the subject's existing teeth.

In another embodiment, the context encoder neural network is a surface-based encoder. A surface-based encoder may have the beneficial effect, that using a surface-based method may allow to directly work with three-dimensional meshes.

In another embodiment, the context encoder neural network is a DiffusionNet encoder.

In another embodiment, the context encoder neural network is a graph-based encoder. A graph-based encoder may have the beneficial effect, that using a graph-based method may allow to directly work with three-dimensional meshes.

In another embodiment, the context encoder neural network is a Graph Neural Network.

In another embodiment, the context encoder neural network is a point-based encoder. A point-based encoder may have the beneficial effect, that using a point-based method may allow to directly work with point clouds. Such point clouds are, e.g., a raw output of three-dimensional scanners.

In another embodiment, the context encoder neural network is a PointNet encoder.

In another embodiment, the context encoder neural network is a voxel-based encoder.

In another embodiment, the context encoder is a three-dimensional ShapeNet.

In another embodiment, the context encoder neural network is a three-dimensional convolutional neural network.

In another embodiment, the context encoder neural network is a multi-view rendering-based method.

In another embodiment, the context encoder neural network is a two-dimensional convolutional neural network.

In another embodiment, the context encoder neural network is an implicit surface-based encoder. An implicit surface-based encoder may have the beneficial effect, that an implicit-surface based method uses implicit surfaces representing a three-dimensional shape at infinite resolution without requiring lots of memory.

In another embodiment, the context encoder neural network is an Occupancy Network.

In another embodiment, the context encoder neural network is an encoder portion of a convolutional autoencoder.

In another embodiment, the one or more teeth of the subject comprise one or more adjacent teeth of the replacement tooth. This embodiment is beneficial, because by taking one or more adjacent teeth the neural network may be able to produce an accurate replacement tooth. Structure and appearance of an adjacent tooth may in general be similar to the replacement tooth. The one or more teeth of the subject of which the one or more three-dimensional digital tooth models are descriptive may, e.g., comprise one adjacent teeth of the replacement tooth. For example, the replacement tooth may be the last or first tooth of the dental arch, e.g., a second molar in absence of an adjacent third molar. For example, adjacent teeth may only be selected, in case they are of the same type as the replacement tooth and the replacement tooth may, e.g., be a first molar, a first or second premolar or a lateral incisor. For example, two or more three-dimensional digital tooth models descriptive of two or more teeth of the subject may be received. For example, the teeth of the subject of which the two or more three-dimensional digital tooth models are descriptive may, e.g., comprise two adjacent teeth of the replacement tooth. For example, adjacent teeth may be selected, regardless of their type of tooth.

In another embodiment, the one or more teeth of the subject comprise a contralateral tooth of the replacement tooth. This embodiment may be particularly beneficial because the structure and appearance of the contralateral tooth should be very similar to the replacement tooth. This may lead to a more accurate replacement or duplication of the replacement tooth.

In another embodiment, the one or more teeth of the subject comprise a group of teeth or a partial dental arch. In this embodiment models of the teeth that make up a group or partial dental arch are used. This may provide more data which may provide for a more accurate modeling of the replacement tooth.

In another embodiment, the one or more teeth comprise one or more antagonist teeth of the replacement tooth. Taking into account symmetries, based on the symmetry between maxillary and mandibular dental arch, each tooth has a symmetric tooth within the opposite dental arch, i.e., antagonist, also referred to as a major antagonist. For example, the one or more teeth may comprise the major antagonist of the replacement tooth. Furthermore, major antagonists of adjacent teeth of the replacement tooth may be taken into account. These antagonists may also be referred to as minor antagonists of the replacement tooth. For example, in addition to the major antagonist of the replacement tooth one or more minor antagonists of the replacement tooth may be comprised. For example, in addition to the major antagonist of the replacement tooth a contralateral tooth of the major antagonist of the replacement tooth may be comprised. Furthermore, one or more contralateral teeth of the minor antagonists of the replacement tooth may be comprised. Taking into account contacts between teeth, two antagonist teeth that are in contact with a tooth may be identified. In view of the contacts, the major antagonist is the tooth with which the respective tooth has the largest area of contact. In the maxilla, the minor antagonist is mesial to the major antagonist, and in the mandible, the minor antagonist is distal to the major antagonist. For example, the one or more teeth may comprise the major antagonist as well as the minor antagonist of the replacement tooth with respect to the contacts between teeth. Using one or both of these as input to the neural network may result in accurate modeling of the replacement tooth.

In another embodiment, the one or more three-dimensional digital tooth models comprise tooth coordinates that are descriptive of a location within the subject's mouth, e.g., within one of the subject's dental arches and/or within one of the subject's jaws. The one or more three-dimensional digital tooth models are individual models of individual teeth. The selection of the replacement tooth may also be labeled or contain information about where this particular tooth is located within the subject's mouth. The one or more three-dimensional digital tooth models may, e.g., result from an intraoral scan of the subject's mouth. The scan may acquire data descriptive of hard and soft tissue structures within the subject's mouth, e.g., of teeth and gingiva. This data may in particular be descriptive of the location within the subject's mouth and be used for providing tooth coordinates of the respective teeth.

For example, the one or more teeth of the subject comprise one or more adjacent teeth of the replacement tooth and/or the one or more teeth of the subject comprise one or more antagonist teeth of the replacement tooth. Specifying the adjacent teeth and/or the antagonist teeth may provide information about where the replacement tooth should go. The tooth generating neural network, e.g., is further configured to output placement coordinates of the replacement tooth in response to receiving the one or more three-dimensional digital tooth models as input. This embodiment may be beneficial because by providing the placement coordinates this may provide a means of automatically positioning the generated three-dimensional digital model in a model of the subject's mouth.

In another embodiment, the tooth model generating neural network is configured to output the placement coordinates of the replacement tooth. In this embodiment the tooth model generating neural network is directly configured to output the placement coordinates of the replacement tooth. For example, the neural network may encode the replacement coordinates. This may be beneficial, because it provides the placement coordinates at the same time that the generated three-dimensional digital model is provided.

In another embodiment, the decoder portion is configured for outputting the placement coordinates. In this embodiment the same decoder portion that is used to generate the generated three-dimensional digital model of the replacement tooth also outputs the placement coordinates. This may be a convenient means of providing these automatically.

In another embodiment, the tooth model generating neural network further comprises a position prediction portion that is configured for outputting the placement coordinates. In this embodiment there is an additional portion or part to the tooth model generating neural network that additionally provides the placement coordinates. The position prediction portion is configured for receiving a concatenation of a tooth feature vector of the one or more adjacent teeth that are descriptive of the tooth coordinates as input. For example, the encoder portion may comprise a tooth-specific context encoder neural network for each of the one or more three-dimensional digital tooth models. In this case each of the tooth-specific context encoder neural networks outputs a tooth feature vector which is then concatenated into the collective feature vector. In this case the position prediction portion, e.g., concatenates two teeth feature vectors for two adjacent teeth of the placement tooth. As the adjacent teeth essentially define where it is possible to place the replacement tooth this is an efficient means of defining its position.

In another embodiment, the position prediction portion comprises one or more connected layers. This embodiment may be beneficial because the one or more connected layers provide essentially a means of combining the coordinates teeth, e.g., of the one or more adjacent teeth, to calculate the placement coordinates as a linear model. This is a highly effective means of determining the placement coordinates.

In another embodiment, the decoder portion is implemented as a decoder of an autoencoder.

In another embodiment, the decoder portion is implemented as a variational autoencoder decoder portion.

In another embodiment, the decoder portion is implemented as an auto decoder.

In another embodiment, the decoder portion is implemented as a generative adversarial network.

In another embodiment, the decoder portion is implemented as a normalizing flow model.

In another embodiment, the decoder portion is implemented as a diffusion model.

In another embodiment, the decoder portion is implemented as an autoregressive model.

For the decoder portion, for each of the exemplary implementations listed above, again any one or more of the neural networks identified as exemplary implementations for the context encoder neural network above may be used. These exemplary neural networks, e.g., comprise any one of the following: a surface based neural network, a DiffusionNet, a graph-based neural network, a Graph Neural Network, a point-based neural network, a PointNet, a voxel based neural network, three-dimensional ShapeNet, a three dimensional convolutional neural network, a multi-view rendering based neural network, a two-dimensional convolution neural network, an implicit surface based neural network, an Occupancy Network, and a decoder portion of a convolutional autoencoder. For example, a generative adversarial network may be implemented using a diffusion net or using a graph neural network.

In another embodiment, the latent space of the decoder portion is regularized. This feature is discussed in the context of a variational autoencoder that also applies to the other types of neural networks which can be used for the decoder portion. In a normal autoencoder the encoding portion produces a latent space vector which is then input into the decoder portion. If there is no regularization of the latent space vector, as its position is changed, the output of the decoder portion may be highly erratic. It is essentially as one changes the position of the latent space vector the results can vary drastically over very short changes in the space of this vector. To obtain a regularized latent space one adds a constraint to the loss function. Typically, the latent space vector will be forced to fit a probability distribution such as a normal distribution. The effect of this is the regularization of the latent space. When this is performed, small changes in the latent space vector result in minor changes in the output of the decoder portion. This may be beneficial in this context because it is then possible to make small changes in the latent space vector and have this result in minor changes in the outputted or generated three-dimensional digital model. This enables changes to be made or optimized.

In another embodiment, the method further comprises iteratively modifying the generated three-dimensional digital model of the replacement tooth by modifying the latent space vector using an optimization to minimize a loss function that enforces interproximal contact with the one or more adjacent teeth of the replacement tooth. This is an example application of when the latent space of the decoder portion is regularized. Because it has been regularized an optimization algorithm can be used to modify the generated three-dimensional digital model such that the interproximal contact with the one or more adjacent teeth is correct. This may for example be achieved by using a back propagation and a gradient descent method. However, other optimization algorithms may be used and the back propagation is only an example.

In another embodiment, the loss function further enforces avoiding occlusal contact of greater than the predefined maximum depth. Thus, occlusal contacts with an antagonist of the replacement tooth may to be equal or less than the predefined maximum depth defining a threshold. This embodiment may be beneficial because it may help the generated three-dimensional digital model of the replacement tooth be adjusted so that it better fits the subject's jaw. For example, a suitable occlusion may thus be achieved for the replacement tooth.

In another embodiment, the loss function further enforces contact with the antagonist tooth of the replacement tooth at predefined landmarks. This embodiment may be beneficial because it also may help to adjust the shape and/or position of the generated three-dimensional digital model of the replacement tooth such that it better fits the subject's jaw. For example, a suitable occlusion may thus be achieved for the replacement tooth.

In another embodiment, the method further comprises receiving a surface modification. The method further comprises applying the surface modification to the generated three-dimensional digital model of the replacement tooth. This embodiment may be beneficial because it may be useful in making or giving the generated three-dimensional digital model a more realistic appearance. The generated three-dimensional digital model is generated using a decoding portion which is controlled by a latent space vector. The latent space vector may do an accurate job of providing the correct shape for the generated three-dimensional digital model. However, the latent space vector has a much lower dimensionality or less information than an actual tooth model does. In general, decoding portions such as the decoding portion of an autoencoder, produce tooth models that are smoother than they are in reality. A result of this is that the tooth or teeth produced by a neural network may have a typically artificial appearance to them. Such teeth models may typically lack the fine surface details or surface roughness that would make a tooth have a highly realistic appearance. Performing the surface modification may be used to modify the surface slightly so that it has the same degree of roughness or texture that a tooth of a subject has.

In another embodiment, the surface modification is received from a database of surface modifications. For example, the surface modifications may be retrieved from a database and, in some instances, the dentist or other technician may try applying different surface modifications till the generated three-dimensional digital model of the replacement tooth has a more realistic appearance.

In another embodiment, the method further comprises receiving an autoencoded three-dimensional digital tooth model in response to inputting a three-dimensional digital model of a selected tooth of the subject into a tooth replicating autoencoder neural network. The tooth replicating autoencoder neural network comprises an autoencoder encoding portion and an autoencoder decoding portion. The autoencoder decoding portion is identical with the decoder portion of the tooth generating neural network. The method further comprises determining the surface modification to morph the autoencoded three-dimensional digital tooth model into the three-dimensional digital model of the selected tooth of the subject.

This embodiment is beneficial, because it is able to produce a highly realistic generated three-dimensional digital model of the replacement tooth that is specific to a particular individual. In this case the autoencoder decoding portion is identical with the decoder portion of the tooth model generating neural network. This means that the latent space for both portions is identical and the smoothing effect, which was mentioned above, by the decoder portion is identical in both cases. A selected tooth was taken from the same individual so the selected tooth will have the same type of surface roughness or topology that the other teeth have. The combination of the two enables a means of copying the surface structure of a tooth to the generated three-dimensional digital model of the subject which fits not only the particular decoder portion of the tooth model generating neural network, but also the specific individual.

For example, such a determining of surface modifications may be executed for a group of subjects and used for compiling a database, i.e., library, of surface modifications. The determined surface modifications may, e.g., be added to the library of surface modifications as they are. The determined surface modifications may, e.g., be adjusted, combined and/or averaged, when being added to the library of surface modifications.

In another embodiment, the selected tooth is a contralateral tooth of the replacement tooth. When the replacement tooth is a contralateral tooth, the method comprises performing a mirror image transform on the surface modification. As the contralateral tooth typically has a very similar appearance and structure to the missing tooth or the replacement tooth this embodiment is highly effective.

In another embodiment, the selected tooth is an adjacent tooth of the replacement tooth.

This embodiment may be beneficial, because teeth which are adjacent to each other may have a very similar surface structure.

In another embodiment, the selected tooth is an antagonist tooth of the replacement tooth. The antagonist tooth may also have a very similar structure to the replacement tooth so this may be highly effective. The method may comprise applying a mirror image transform to the surface modification of the antagonist tooth.

In another embodiment, the decoder portion is configured to output the generated three-dimensional digital model by morphing a canonical-shaped mesh into the generated three-dimensional digital model of the replacement tooth. In this embodiment the decoder portion is essentially configured such that it outputs a generated three-dimensional digital model with a particular topology of the vertices and connections between these vertices. The canonical-shaped mesh may take different forms in different examples. For example, the canonical-shaped mesh may be a sphere or other shape. The decoder portion is then configured to modify this particular shape into the generated three-dimensional digital model.

The use of a canonical-shaped mesh may be useful when doing style transfer, because changes in one mesh can be applied to another mesh without problem. For example, this canonical structure can be used by the tooth replicating autoencoder neural network. The surface modification used to morph the autoencoded three-dimensional digital tooth model into the three-dimensional digital model can be essentially coordinates for particular vertices and how they are moved such that the autoencoded three-dimensional digital tooth model matches that of the selected tooth of the subject. These coordinate changes may then be the surface modification. When performing the surface modification on the generated three-dimensional digital model, these changes in the location of the vertices can simply be applied as a vector operation. This may be a highly effective means of causing small surface changes in the generated three-dimensional digital model that result in a realistic tooth.

In another embodiment, the method further comprises acquiring a three-dimensional digital dental structure of the subject using a three-dimensional imaging system. For example, a three-dimensional camera may be used to image the contents of a subject's mouth intraorally, and this may be used to provide the three-dimensional digital dental structure. Alternatively, an impression of the subject's dental structure, i.e., a negative of the respective dental structure, may be acquired and either scanned directly using a three-dimensional camera or used to provide a dental cast, i.e., a positive of the respective dental structure, which is scanned using the three-dimensional camera for providing the three-dimensional digital dental structure. In other examples, other tomographic imaging techniques such as computed tomography or even magnetic resonance imaging may be used for acquiring the three-dimensional digital dental structure. The computed tomography is used more often because computed tomography has an easier time in imaging bony structures.

In another embodiment, the one or more three-dimensional digital tooth models are selected from a segmentation of the three-dimensional digital dental structure using a predetermined criterion. The predetermined criterion could be different in different examples. In one example, the user or a protocol is used to select the one or more three-dimensional digital tooth models based on their spatial relationship to the replacement tooth, for which a three-dimensional digital model is to be generated. In another example, the predetermined criterion is determined by the position of the teeth relative to the replacement tooth based on what was used for training the tooth model generating neural network. For example, the specification of a replacement tooth may then be used to select a particular tooth model generating neural network that is trained for replacing just that specific tooth or a particular type of tooth, such as a molar or other type of tooth. This tooth model generating neural network was trained using a specific type of input. For example, particular tooth models with a spatial relationship to the replacement tooth. This information about which model should be input based on the training may then be used for the predetermined criterion.

The segmentation of the three-dimensional digital dental structure may, e.g., result in a plurality of three-dimensional digital tooth models, from which the one or more three-dimensional digital tooth models to be used for generating the three-dimensional digital model of the replacement tooth are selected using the predetermined criterion.

Furthermore, the segmentation of the three-dimensional digital dental structure may, e.g., result in a three-dimensional digital model of the gingiva, in which the teeth described by the plurality of three-dimensional digital tooth models are arranged.

The segmentation of the three-dimensional digital dental structure may be performed using a segmentation module. Various means may be used for performing the segmentation. In one example a shape deformable segmentation module is used where a preexisting and elastic model of the teeth are fit to the three-dimensional digital dental structure. In another example, the segmentation module can be implemented as a neural network that is trained to receive the three-dimensional digital dental structure and output meshes representing the individual teeth and optionally the gingiva.

In another embodiment, the method further comprises rendering a display of a set of one or more three-dimensional digital tooth models of the subject including the generated three-dimensional digital model of the replacement tooth. In this embodiment the generated three-dimensional digital model of the replacement tooth is rendered with the other three-dimensional digital tooth models of the subject. This may for example provide a means of showing the subject, dentist, dental technician, or other operator the result of the generated three-dimensional digital model with the other teeth of the subject. This may for example be used for approving or disapproving of the replacement tooth as well as a preliminary step in having a dental restoration prepared.

In another embodiment, the method further comprises fabricating a dental restoration model using the generated three-dimensional digital model of the replacement tooth. The dental restoration may, e.g., be a crown, an inlay, an onlay, or an overlay.

In another embodiment, the method further comprises fabricating a replacement crown model using the generated three-dimensional digital model of the replacement tooth.

In another embodiment, the method further comprises fabricating an inlay model using the generated three-dimensional digital model of the replacement tooth.

In another embodiment, the method further comprises fabricating an onlay model using the generated three-dimensional digital model of the replacement tooth.

In another embodiment, the method further comprises fabricating an overlay model using the generated three-dimensional digital model of the replacement tooth.

In all of these embodiments, where the dental restoration model, e.g., the replacement crown model, the inlay model, the onlay model, or the overlay model, is fabricating, the generated three-dimensional digital model may be used to provide data to a machine for fabricating this replacement or dental restoration. For example, the generated three-dimensional digital model of the replacement tooth may be used as a template for fabricating the dental restoration model with the dental restoration model being a physical copy of at least a part of the respective template. For example, data can be sent to a machining device, a three-dimensional printing device, or a casting device which can be used to perform this fabricating step. The casting device may, e.g., comprise a machining device and/or three-dimensional printing device for fabricating a casting mold, which is used, e.g., by the casting device for casting the dental restoration.

In another aspect the invention provides for a dental system. The system comprises a memory storing machine-executable instructions and a tooth model generating neural network. The tooth model generating neural network comprises an encoder portion and a decoder portion. The encoder portion is configured for outputting a collective feature vector of one or more digital tooth models. The tooth model generating neural network further comprises at least one fully connected layer configured to output a latent space vector in response to receiving the collective feature vector. The decoder portion is configured to output a generated three-dimensional digital model of the replacement tooth in response to receiving the latent space vector.

The dental system further comprises a computational system. Execution of the machine-executable instructions causes the computational system to receive a selection of a replacement tooth for a subject. Execution of the machine-executable instructions further causes the computational system to receive one or more three-dimensional digital tooth models descriptive of one or more teeth of the subject. Execution of the machine-executable instructions further causes the computational system to receive the generated three-dimensional digital model of the replacement tooth in response to inputting the one or more three-dimensional digital tooth models descriptive of the one or more teeth of the subject into the tooth model generating neural network. The advantages of this have been previously discussed.

The dental system may be configured for executing any of the aforementioned examples of the dental method.

In another embodiment, the dental system further comprises a fabrication system configured to fabricate a dental restoration model using the generated three-dimensional digital model of the replacement tooth. The dental restoration model may, e.g., be any one of the following: a replacement crown model, an inlay model, an overlay model, and an onlay model.

The fabrication system could for example be an automated or CNC machining system, a three-dimensional printer, or an automatic casting system. In some examples the machining system or the three-dimensional printing system may be used in the process of fabricating a mold for the casting process.

In another aspect the invention provides for a computer program that comprises machine-executable instructions and a tooth model generating neural network. The computer program may for example be stored on a non-transitory storage medium. The tooth model generating neural network comprises an encoder portion and a decoder portion. The encoder portion is configured for outputting a collective feature vector descriptive of the one or more digital tooth models. The tooth model generating neural network further comprises at least one fully connected layer configured to output a latent space vector in response to receiving the collective feature vector. The decoder portion is configured to output the generated three-dimensional digital model of the replacement tooth in response to receiving the latent space vector.

Execution of the machine-executable instructions causes the computational system to receive a selection of a replacement tooth for a subject. Execution of the machine-executable instructions further causes the computational system to receive one or more three-dimensional digital tooth models descriptive of one or more teeth of the subject. Execution of the machine-executable instructions further causes the computational system to receive the generated three-dimensional digital model of the replacement tooth in response to inputting the one or more three-dimensional digital tooth models descriptive of one or more teeth of the subject into the tooth model generating neural network. The advantages of this have been previously discussed.

The computer program may, e.g., be configured for executing any of the aforementioned examples of the dental method.

In another aspect the invention provides for a dental method. The method comprises receiving a generated three-dimensional digital model of the replacement tooth of the subject. The method further comprises receiving a three-dimensional digital model of a selected tooth of the subject. The method then further comprises receiving an autoencoded three-dimensional digital tooth model in response to inputting the three-dimensional digital model of the selected tooth of the subject into an autoencoder neural network. The autoencoder neural network comprises an autoencoder portion and an autoencoder decoding portion. The method further comprises determining a surface modification to morph the autoencoded three-dimensional digital tooth to the selected tooth of the subject. The method further comprises applying the surface modification to the generated three-dimensional digital model of the replacement tooth.

This method may be beneficial because it may provide for a means of making a generated three-dimensional digital model of a replacement tooth of the subject more similar to an actual tooth of the subject. A typical problem with generated digital models of teeth is that they have a tendency to be smoother than actual or real teeth are. For example, the teeth may lack small amounts of detail such as a texture or fine three-dimensional structure.

In another embodiment, the selected tooth is a contralateral tooth of the replacement tooth. If the selected tooth is a contralateral tooth, then a mirror image transformation might be applied to the surface modification before it is used to modify the generated three-dimensional digital model of the replacement tooth. Using a contralateral tooth of the replacement tooth may have the beneficial effect, that the contralateral tooth may define a suitable surface structure for the replacement tooth, due to the symmetries within the dental arches of a human.

In another embodiment, the selected tooth is an adjacent tooth of the replacement tooth. Using an adjacent tooth of the replacement tooth may have the beneficial effect, that the adjacent tooth may define a suitable surface structure for the replacement tooth. This may in particular be the case, if the adjacent tooth is of the same type as the replacement tooth.

In another embodiment, the replacement tooth is an antagonist of the replacement tooth. If the chosen tooth is an antagonist, then in some examples, the method may further comprise applying a mirror image transformation to the surface modification before it is used to modify the generated three-dimensional digital model of the replacement tooth. Using an antagonist of the replacement tooth may have the beneficial effect, that the antagonist may define a suitable surface structure for the replacement tooth, due to the symmetry between the two dental arches of a human.

The method further comprises receiving the selection of the replacement tooth for the subject. The method further comprises receiving one or more three-dimensional digital tooth models descriptive of one or more teeth of the subject. The method further comprises receiving the generated three-dimensional digital model of the replacement tooth of the subject in response to inputting the one or more three-dimensional digital tooth models into a tooth model generating neural network. The tooth model generating neural network comprises an encoder portion and a decoder portion. The decoder portion is identical with the autoencoder decoding portion. The encoder portion is configured for outputting a collective feature vector descriptive of the one or more teeth of the subject.

The generating neural network further comprises at least one fully connected layer configured to output a latent space vector in response to receiving the collective feature vector. The decoder portion is configured to output the three-dimensional digital model in response to receiving the latent space vector.

In another embodiment, the generated three-dimensional digital model of a replacement tooth is received from a database of generated three-dimensional digital tooth models, e.g., a tooth library. In the above embodiment the generated three-dimensional digital model is generated by the tooth model generating neural network. This embodiment is an alternative. For example, there may be a large library or database which contains a large number of generated three-dimensional digital models. These may for example be fit into the location of the subject, but they may lack the same surface structure and fine details that the subject's real teeth possess. Such differences regarding the surface structure and/or fine details may, e.g., be due to a subject-individual wear of the subject's real teeth. This embodiment provides a means of using a library tooth as a replacement tooth and then modifying this library tooth such that it has an appearance of a natural tooth of the subject.

In another embodiment, the decoder portion is configured to generate the generated three-dimensional digital model of the replacement tooth by nnorphing a canonical-shaped mesh. The use of a canonical-shaped mesh may be beneficial because, as was described above, it provides a standard number of vertices and relationship between these vertices. The first surface modification may therefore then just be instructions on how to translate various vertices of a canonical-shaped mesh. It may provide for a standardized way of performing a surface modification on a three-dimensional digital model of a tooth.

In another embodiment, the canonical mesh comprises vertices. The surface modification is determined by calculating a transformation of the vertices of the three-dimensional digital model of a selected tooth along normals until they intersect the autoencoded three-dimensional digital tooth model. This may for example provide a standardized way of modifying a canonical mesh. For example, the normals are vertex normals, i.e., directional vectors associated with the vertices, intended as a replacement to the true geometric normals of the surfaces defined by the mesh. These vertex normals may be computed as normalized averages of surface normals of the surfaces defined by the mesh, which contain the respective vertex. The averages may, e.g., be weighted for example by the area of the surface or they may be unweighted. For determining the intersections with the autoencoded three-dimensional digital tooth model, the autoencoded three-dimensional digital tooth model may, e.g., be overlaid over the three-dimensional digital model of a selected tooth.

In another embodiment, the surface modification is determined by a displacement mapping between the three-dimensional digital model of the selected tooth and the autoencoded three-dimensional digital tooth model. A displacement mapping as used herein, indicates a displacement of the surface of the tooth. Providing the displacement mapping may also be an effective means of adding fine structure or texture to a three-dimensional digital tooth model.

In another aspect the invention provides for a dental system. The dental system comprises a memory storing machine-executable instructions. The dental system further comprises a computational system. Execution of the machine-executable instructions causes the computational system to receive a generated three-dimensional digital model of a replacement tooth of a subject. Execution of the machine-executable instructions further causes the computational system to receive a generated three-dimensional digital model of the replacement tooth of the subject. Execution of the machine-executable instructions further causes the computational system to receive an autoencoded three-dimensional digital tooth model in response to inputting the three-dimensional digital model of the selected tooth of the subject into an autoencoder neural network. The autoencoder neural network comprises an autoencoder encoding portion and an autoencoder decoding portion.

Execution of the machine-executable instructions further causes the computational system to determine a surface modification to morph the autoencoded three-dimensional digital tooth to the selected tooth of the subject. Execution of the machine-executable instructions further causes the computational system to apply the surface modification to the generated three-dimensional digital model of the replacement tooth.

The dental system may be configured for executing any of the aforementioned examples of the dental method.

In another embodiment, the dental system further comprises a fabrication system configured to fabricate a dental restoration model using the generated three-dimensional digital model of the replacement tooth that has the applied surface modification applied to it. The dental restoration model may, e.g., be any one of the following: a replacement crown model, an inlay model, an overlay model, and an onlay model.

In another aspect the invention provides for a computer program comprising machine-executable instructions. The computer program may for example be stored on a non-transitory storage medium. Execution of the machine-executable instructions causes a computational system to receive a generated three-dimensional digital model of a replacement tooth of the subject. Execution of the machine-executable instructions further causes the computational system to receive a three-dimensional digital model of the selected tooth of the subject. Execution of the machine-executable instructions further causes the computational system to receive an autoencoded three-dimensional digital tooth model in response to inputting the three-dimensional digital model of the selected tooth of the subject into an autoencoder neural network. The autoencoder neural network comprises an autoencoding portion and an autoencoder decoding portion.

Execution of the machine-executable instructions further causes the computational system to determine a surface modification to morph the autoencoded three-dimensional digital tooth to the selected tooth of the subject. Execution of the machine-executable instructions further causes the computational system to apply the surface modification to the generated three-dimensional digital model of the replacement tooth.

The computer program may be configured for executing any of the aforementioned examples of the dental method.

In another aspect the invention provides for a dental method. The method comprises receiving a generated three-dimensional digital model of a replacement tooth of the subject. The generated three-dimensional digital model is formed from a mesh with a mesh topology comprising vertices. The method further comprises receiving a surface modification to be transferred to the mesh forming the generated three-dimensional digital model. The surface modification is defined for the same mesh topology as the mesh forming the generated three-dimensional digital model and comprises a location adjustment for the vertices of the mesh topology. The method further comprises applying to the surface modification to the mesh forming the generated three-dimensional digital model of the replacement tooth. In this embodiment, this may mean using the location adjustment to change the position of the vertices of the generated three-dimensional digital model of the replacement tooth of the subject.

This method may be beneficial because it may provide for an advantageous means of making a generated three-dimensional digital model of a replacement tooth for the subject more similar to an actual tooth of the subject by transferring a surface modification to the mesh forming the generated three-dimensional digital model of the replacement tooth. The surface modification defines location adjustment for the vertices of the mesh topology of the mesh forming the generated three-dimensional digital model of the replacement tooth. A typical problem with generated digital models of teeth is that they may, e.g., have a tendency to be smoother than actual or real teeth are or such models may have a fine-structure not matching the fine-structure of other teeth of the subject. For example, the teeth may lack small amounts of detail such as a texture or fine three-dimensional structure or they may differ in these small amounts of detail.

The received surface modification to be transferred to the mesh forming the generated three-dimensional digital model may be surface modifications defined for a particular mesh topology of the vertices and connections between these vertices, which is identical with the mesh topology of the mesh forming the generated three-dimensional digital model of the replacement tooth. Thus, because modifications, like surface modifications, defined for one mesh may easily be applied to the mesh with the same topology. The surface modification used may be essentially coordinates for particular vertices and how they are moved. When performing the surface modification on the generated three-dimensional digital model of the replacement tooth, these changes in the location of the vertices can simply be applied as a vector operation. This may be a highly effective means of causing small surface changes in the generated three-dimensional digital model of the replacement tooth that result in a realistic tooth.

In another embodiment, the surface modification is received from a database of surface modifications. In this example for example a library of three-dimensional digital models of teeth may be used and one these library models selected to provide for a replacement tooth. This however may have a surface which does not match that of the subject well. Applying the surface modification may provide for an improved means of providing a realistic looking replacement tooth for a subject.

In another embodiment, the method further comprises receiving an autoencoded three-dimensional digital tooth model in response to inputting a three-dimensional digital model of a selected tooth of the subject into a tooth replicating autoencoder neural network. The tooth replicating autoencoder neural network comprises an autoencoder encoding portion and an autoencoder decoding portion. The autoencoder decoding portion is identical with the decoder portion of the tooth model generating neural network. The method further comprises determining the surface modification to morph the autoencoded three-dimensional digital tooth model into the three-dimensional digital model of the selected tooth of the subject.

In another embodiment, the selected tooth is a contralateral tooth. If the selected tooth is a contralateral tooth, then the method may further comprise applying a mirror image transformation to the surface modification. In another embodiment, the selected tooth is an adjacent tooth of the replacement tooth.

In another embodiment, the selected tooth is an antagonist tooth of the replacement tooth. If the selected tooth is the antagonist tooth, then the method may further comprise applying a mirror image transformation to the surface modification.

In another aspect the invention provides for a dental system. The dental system comprises a memory storing machine-executable instructions. The dental system further comprises a computational system. Execution of the machine-executable instructions causes the computational system to receive a generated three-dimensional digital model of a replacement tooth of a subject. The generated three-dimensional digital model is formed from a mesh with a mesh topology comprising vertices. Execution of the machine-executable instructions further causes the computational system to receive a surface modification to be transferred to the mesh forming the generated three-dimensional digital model. The surface modification is defined for the same mesh topology as the mesh forming the generated three-dimensional digital model and comprises a location adjustment for the vertices of the mesh topology. Execution of the machine-executable instructions further causes the computational system to apply the surface modification to the mesh forming the generated three-dimensional digital model of the replacement tooth.

The dental system may be configured for executing any of the aforementioned examples of the dental method.

In another embodiment, the dental system further comprises a fabrication system configured to fabricate a dental restoration model using the generated three-dimensional digital model of the replacement tooth. The fabrication system may for example include such things as a CNC or automated machining system, a three-dimensional printer, or a system for preparing castings. The dental restoration model may, e.g., be any one of the following: a replacement crown model, an inlay model, an overlay model, and an onlay model.

In another aspect the invention provides for a computer program that comprises machine-executable instructions. The computer program may for example be stored on a non-transitory storage medium. Execution of the machine-executable instructions causes a computational system to receive a generated three-dimensional digital model of the replacement tooth of a subject. The generated three-dimensional digital model is formed from a mesh with a mesh topology comprising the vertices. Execution of the machine-executable instructions further causes the computational system to receive a surface modification to be transferred to the mesh forming the generated three-dimensional digital model. The surface modification is defined for the same mesh topology as the mesh forming the generated three-dimensional digital model and comprises a location adjustment for the vertices of the mesh topology. Execution of the machine-executable instructions further causes the computational system to apply the surface modification to the mesh forming the generated three-dimensional digital model of the replacement tooth.

The computer program may be configured for executing any of the aforementioned examples of the dental method.

It is understood that one or more of the aforementioned embodiments of the invention may be combined as long as the combined embodiments are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor or computational system of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the computational system of the computing device. Examples of computer-readable storage media include, but are not limited to: a floppy disk, a magnetic hard disk drive, a solid-state hard disk, flash memory, a USB thumb drive, Random Access Memory (RAM), Read Only Memory (ROM), an optical disk, a magneto-optical disk, and the register file of the computational system. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example, data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a computational system. 'Computer storage' or 'storage' is a further example of a computer-readable storage medium. Computer storage is any non-volatile computer-readable storage medium. In some embodiments computer storage may also be computer memory or vice versa.

A 'computational system' as used herein encompasses an electronic component which is able to execute a program or machine executable instruction or computer executable code. References to the computational system comprising the example of "a computational system" should be interpreted as possibly containing more than one computational system or processing core. The computational system may for instance be a multi-core processor. A computational system may also refer to a collection of computational systems within a single computer system or distributed amongst multiple computer systems. The term computational system should also be interpreted to possibly refer to a collection or network of computing devices each comprising a processor or computational systems. The machine executable code or instructions may be executed by multiple computational systems or processors that may be within the same computing device or which may even be distributed across multiple computing devices.

Machine executable instructions or computer executable code may comprise instructions or a program which causes a processor or other computational system to perform an aspect of the present invention. Computer executable code for carrying out operations for aspects of the present invention may be written in any combination of one or more programming languages, including an object-oriented programming language such as Java, Smalltalk, C++ or the like and conventional procedural programming languages, such as the "C" programming language or similar programming languages and compiled into machine executable instructions. In some instances, the computer executable code may be in the form of a high-level language or in a pre-compiled form and be used in conjunction with an interpreter which generates the machine executable instructions on the fly. In other instances, the machine executable instructions or computer executable code may be in the form of programming for programmable logic gate arrays.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a computational system of a general-purpose computer, special purpose computer, or other programmable data processing apparatus to produce a machine, such that the instructions, which execute via the computational system of the computer or other programmable data processing apparatus, create means for implementing the functions/acts specified in the flowchart and/or block diagram block or blocks.

These machine executable instructions or computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The machine executable instructions or computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer to indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the computational system of a computer system to interact with and/or control an external computing device and/or apparatus. A hardware interface may allow a computational system to send control signals or instructions to an external computing device and/or apparatus. A hardware interface may also enable a computational system to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

BRIEF DESCRIPTION OF THE DRAWINGS

In the following embodiments of the invention are explained in greater detail, by way of example only, making reference to the drawings in which.

DETAILED DESCRIPTION

Like numbered elements in these figures are either equivalent elements or perform the same function. Elements which have been discussed previously will not necessarily be discussed in later figures if the function is equivalent.

Figure 1:
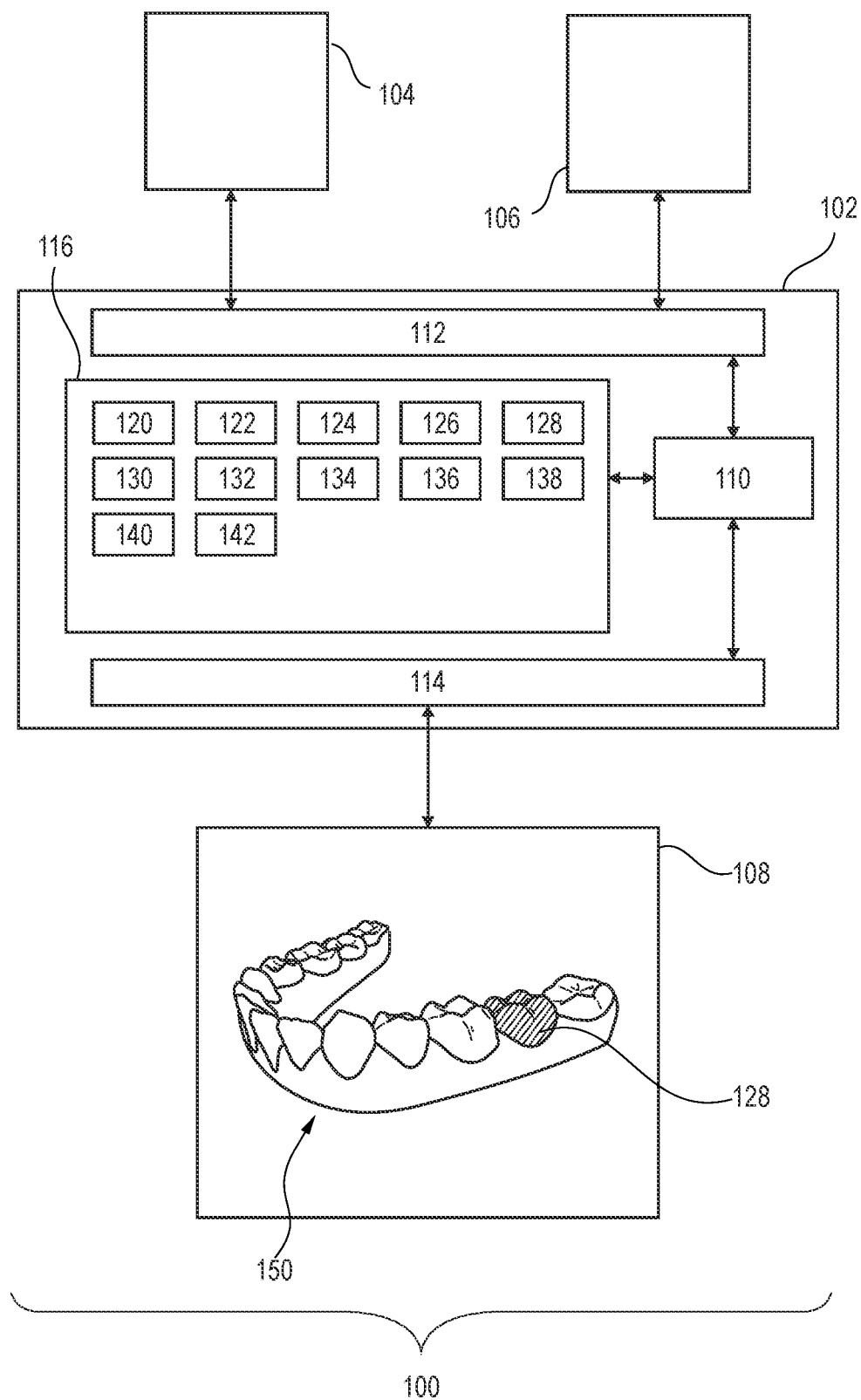
FIG. 1 illustrates an example of a dental system.

FIG. 1 illustrates an example of a dental system 100. The dental system 100 is shown as comprising a computer 102 as well as an optional digital model source 104 and an optional fabrication system 106. The computer 102 is also shown as comprising an optional display 108. The digital model source 104 may for example be a library which provides digital models or, in other examples, it may be an optical or other medical scanner for obtaining measured three-dimensional models from a subject.

The computer 102 is intended to represent one or more computing systems or computers at one or more locations. The computer 102 is shown as containing a computational system 110. Likewise, the computational system 110 is intended to represent one or more computational systems or cores that are located at one or more locations. The computational system 110 is shown as being in communication with an optional hardware interface 112 and an optional user interface 114. The hardware interface 112 enables the computational system 110 to control and communicate with other components of the dental system 100. In some cases, this is a specialized hardware interface 112 or it may also be a network interface, which then allows the computational system 110 to communicate with other components remotely via a network or internet connection.

The user interface 114 enables the operator or user of the dental system 100 to interact with and/or control the dental system 100. In this example, the user interface 114 is shown to comprise the optional display 108.

The computational system 110 is shown as being in communication with a memory 116.

The memory 116 is intended to represent various types of memory which may be accessible to the computational system 110. In some examples, the memory 116 is a non-transitory storage medium.

The memory 116 is shown as containing machine-executable instructions 120. The machine-executable instructions 120 enable the computational system 110 to perform various data processing and numerical tasks as well as to control other components of the dental system 100. The memory 116 is further shown as containing a tooth model generating neural network 122. The memory 116 is further shown as containing a selection of a replacement tooth 124. The memory 116 is further shown as containing one or more three-dimensional digital tooth models 126. They may for example have been received from the digital model source 104. The memory 116 is further shown as containing a generated three-dimensional digital model of the replacement tooth that was received in response to inputting the one or more three-dimensional digital tooth models 126 into the tooth model generating neural network 122.

The tooth model generating neural network 122 may be configured or trained in several different ways. In one case the tooth model generating neural network 122 could be trained such that it is able to take a variety of one or more three-dimensional digital tooth models 126 as input and then output different types of teeth. Another option would be for each particular tooth or tooth type there is an optional collection of tooth model generating neural networks 130. For the specific tooth or tooth type the generated three-dimensional digital model of the replacement tooth 128 can be selected.

In some instances, the generated three-dimensional digital model of the replacement tooth 128 is configured to optionally output placement coordinates of the generated three-dimensional digital model of the replacement tooth also. The memory 116 is shown as optionally containing the placement coordinates 132.

In some examples, the tooth model generating neural network 122 may have a regularized latent space. In this case, the latent space vector can be modified continuously and the generated three-dimensional digital model of the replacement tooth 128 can be modified continuously by modifying this latent space vector. The memory 116 is further shown as containing an optional optimization algorithm 134 that may be used to control this modification of the latent space vector. This for example, can be used to modify the tooth so that it better fits the space between adjacent and antagonist teeth.

The memory 116 is further shown as containing an optional surface modification. When a neural network is used to generate a generated three-dimensional digital model of the replacement tooth 128 it will typically be smoother than a real tooth is. The surface modification may be a modification used to texture and add structure to the surface so that the generated three-dimensional digital model of the replacement tooth 128 has a more realistic or natural appearance. The memory 116 is further shown as containing an optional surface modified generated three-dimensional digital model of the replacement 138. This is the generated three-dimensional digital model of the replacement tooth 128 after its surface has been modified or textured using the surface modification 136.

After the generated three-dimensional digital model of the replacement tooth 128 has been provided it may be used for a variety of different purposes. The memory 116 is further shown as containing an optional computer-aided design module 140. The computer-aided design module 140 takes as input the generated three-dimensional digital model of the replacement tooth 128 and uses this to generate control commands 142 for the fabrication system 106. The fabrication system 106 may then for example be used to fabricate a dental restoration model, like, e.g., a replacement crown model, an inlay model, an overlay model, or an onlay model. The fabrication system could for example be a computer-controlled machining system, a three-dimensional printer, or a casting system.

The display 108 is shown as optionally rendering a set of one or more three-dimensional digital tooth models 150 with the generated three-dimensional digital model of the replacement tooth 128. This rendering or display 108 may be beneficial because the operator or even the dentist may be able to see the generated three-dimensional digital model of the replacement tooth 128 in the context of the subject's other teeth.

Figure 2:
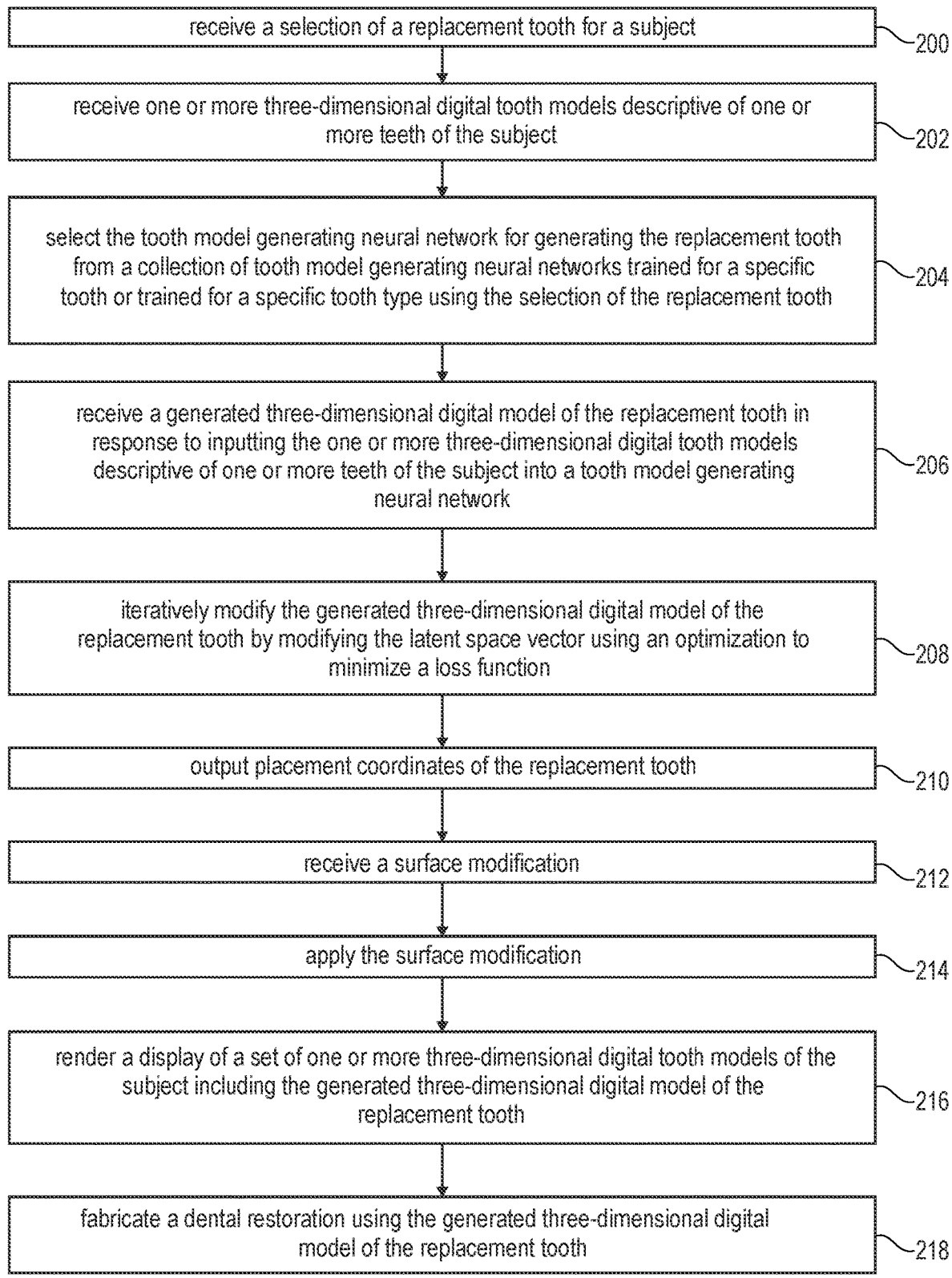
FIG. 2 shows a flow chart which illustrates a method of operating the dental system of FIG. 1.

FIG. 2 shows a flowchart which illustrates a method of operating the dental system 100 of FIG. 1. First, in step 200, the selection of the replacement tooth 124 is received. Next, in step 202, the one or more three-dimensional digital tooth models 126 are received. After step 202, step 204 may be optionally performed. In step 204 the tooth model generating neural network 122 is selected from a collection of tooth model generating neural networks 130. After this step, the generated three-dimensional digital model of the replacement tooth 128 is received in response to inputting the one or more three-dimensional digital tooth models 126 into the tooth model generating neural network 122. After step 206, step 208 may be optionally performed.

In step 208 the generated three-dimensional digital model of the replacement tooth 128 is iteratively modified by modifying the latent space vector using an optimization to minimize a loss function. This may for example be performed using the optimization algorithm 134. The restrictions of when this is applicable were discussed above. Step 210 is performed next and is optional. In step 210 the placement coordinates 132 are output from the tooth model generating neural network 122. After this step, step 212 is optionally performed. In step 212 a surface modification 136 is received. After this, step 214 may be optionally performed. In step 214 the surface modification 136 is applied to the generated three-dimensional digital model of the replacement tooth 128 to produce the surface modified generated three-dimensional digital model of the replacement tooth 138. After this, steps 216 may be optionally performed.

In step 216 a set of one or more three-dimensional digital tooth models 150 of the subject is rendered along with the generated three-dimensional digital model of the replacement tooth 128. After step 216 is performed, step 218 is optionally performed. In step 218 a dental restoration, such as a crown or other implant or overlay, may be manufactured using the generated three-dimensional digital model of the replacement tooth.

Figure 3:
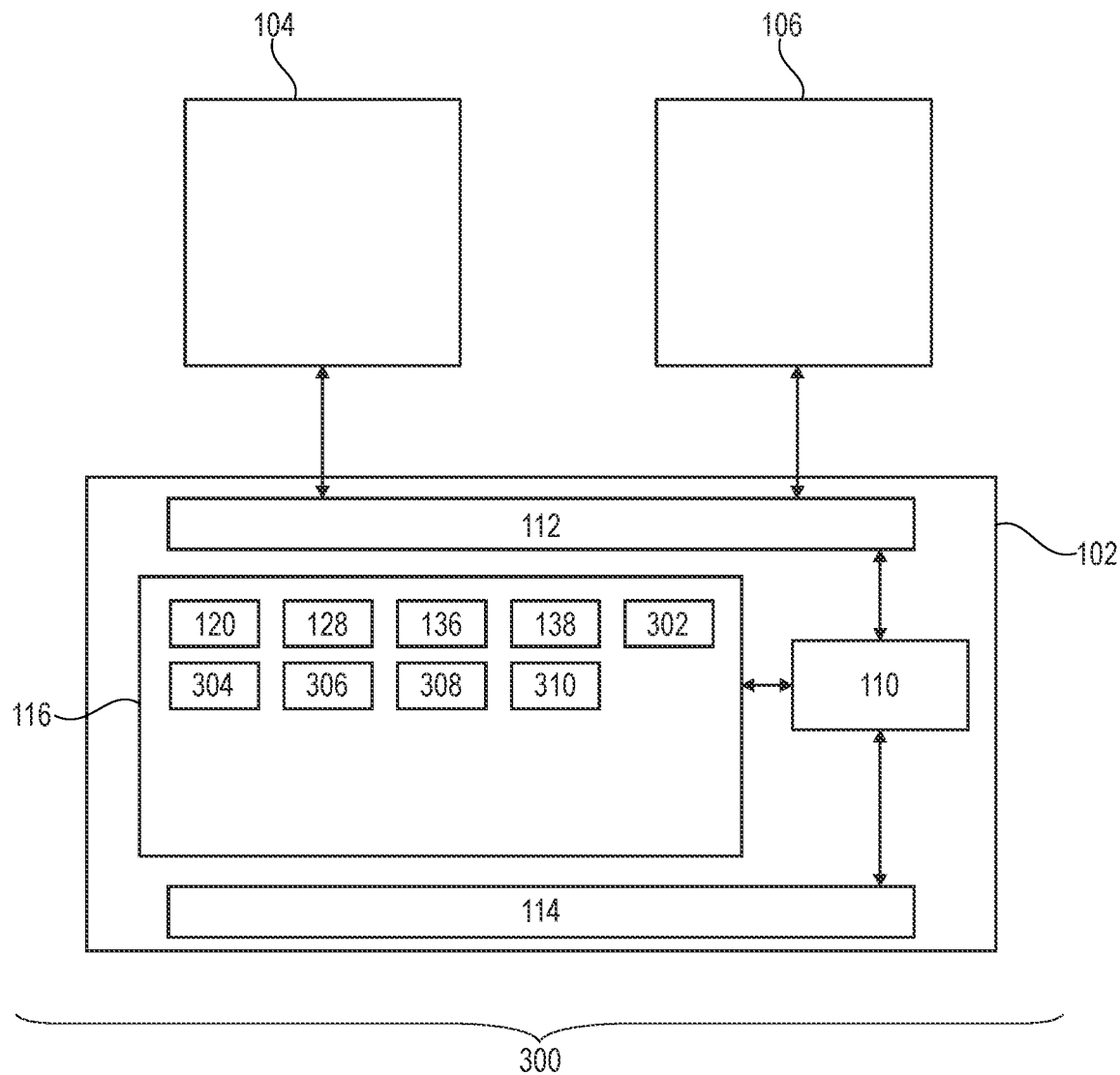
FIG. 3 illustrates a further example of a dental system.

FIG. 3 illustrates a further example of a dental system 300. The dental system is shown as comprising the computer 102 as well as optionally the digital model source 104 and the fabrication system 106. In this example, the memory 116 is shown as containing machine-executable instructions 120. Again, these machine-executable instructions 120 enable the computational system 110 to perform various computational and numerical tasks as well as possible control of the digital model source 104 and the fabrication system 106.

The memory 116 is further shown as containing the generated three-dimensional digital model of the replacement tooth 128 as well as the surface modification 136 and the surface modified generated three-dimensional digital model of the replacement tooth 138. The memory 116 is further shown as containing a three-dimensional digital model of a selected tooth 302. The memory is further shown as containing an autoencoder neural network 304. The memory is further shown as containing an autoencoded three-dimensional digital tooth model 306 that was created by inputting the three-dimensional digital model of a selected tooth 302 into the autoencoder neural network 304. As an alternative to using the digital model source 104, there may be a library of three-dimensional digital tooth models 308. The memory is further shows as containing an optional database of surface modifications 310. One was of providing a surface modification would be to save them after they had been created and they reuse them for other teeth.

Figure 4:
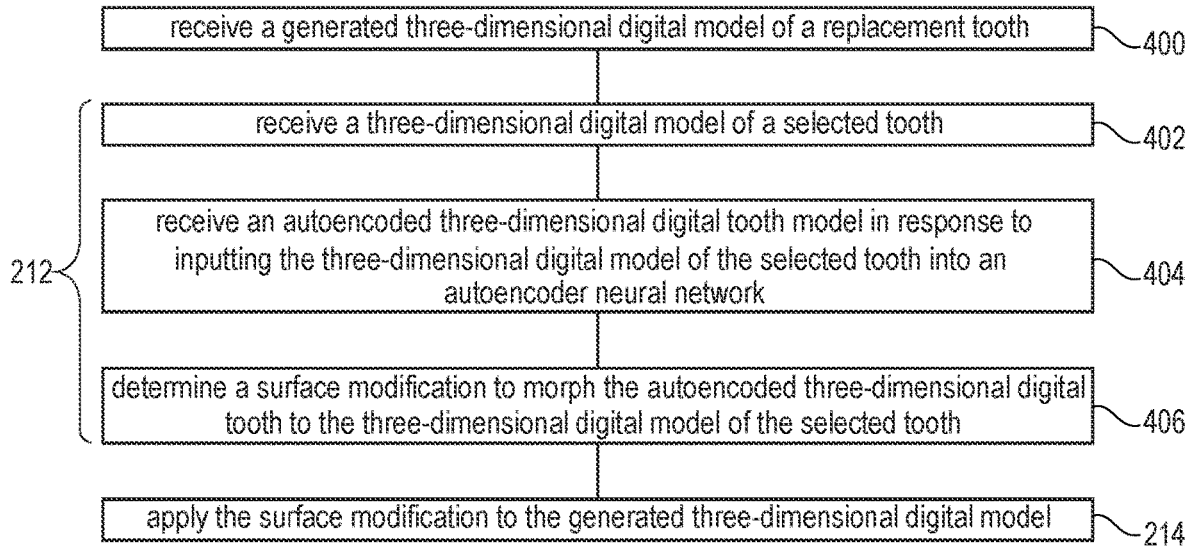
FIG. 4 shows a flow chart which illustrates a method of operating the dental system of FIG. 3.

FIG. 4 illustrates a method of using the dental system 300 of FIG. 3. First, in step 400, a generated three-dimensional digital model of a replacement tooth 128 is received. This may be received for example from the digital model source 104 or from the library of three-dimensional digital tooth models. Next, in step 402, the three-dimensional model of a selected tooth 302 is received. Next, in step 404, the autoencoded three-dimensional digital tooth model 306 is received in response to inputting the three-dimensional digital model of the selected tooth 302 into the autoencoder neural network 304. Next, in step 406, the surface modification 136 is determined which is able to morph the autoencoded three-dimensional digital tooth model 306 to the three-dimensional digital model of the selected tooth. Then finally, in step 214, the surface modification 136 is applied to the generated three-dimensional digital model of a replacement tooth 128.

Figure 5:
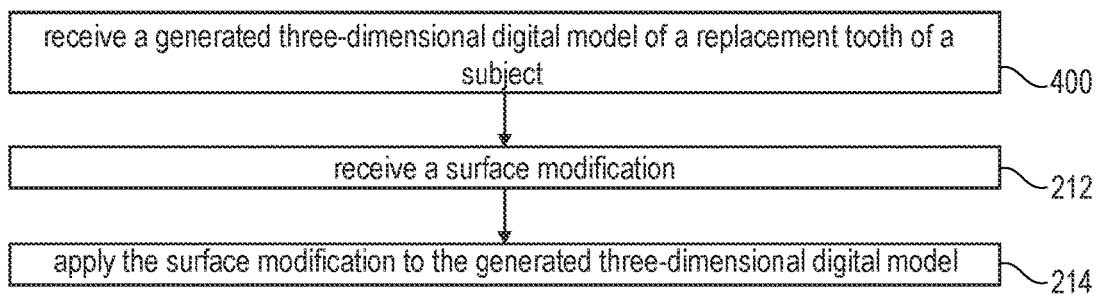
FIG. 5 shows a flow chart which illustrates a method of operating the dental system of FIG. 3.

FIG. 5 shows a further method of using the dental system 300. First, in step 400, the generated three-dimensional digital model of a replacement tooth 128 is received. This may either be from the library 308 or from the digital model source 104. Next in step 212, the surface modification 136 is received. This may either be received as was disclosed in FIG. 4 or it may be received from the database of surface modifications 310, which is located in the memory 116. The method then proceeds to step 214, where the surface modification 136 is applied to the generated three-dimensional digital model of the replacement tooth 128.

It should be noted that the methods of FIGS. 4 and/or 5 may be combined with the method illustrated in FIG. 2. Likewise, the features of FIG. 3 may be combined with the features of FIG. 1.

Figure 6:
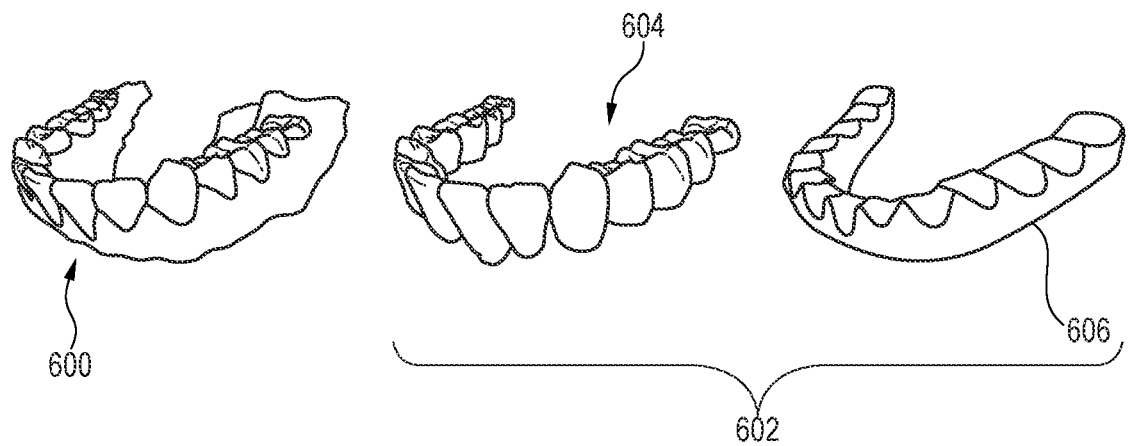
FIG. 6 illustrates an example of a three-dimensional digital dental structure.

FIG. 6 illustrates an example of a three-dimensional digital dental structure 600. The three-dimensional digital dental structure 600 in this example is a three-dimensional model of the subject's teeth using an optical scanner. Adjacent to the three-dimensional digital dental structure 600 is shown a segmentation 602. The segmentation comprises three-dimensional digital tooth models 604 and the gingiva 606. It can be seen that the three-dimensional digital tooth model 604 provides an individual model or three-dimensional model for each tooth that was segmented.

Figure 7:
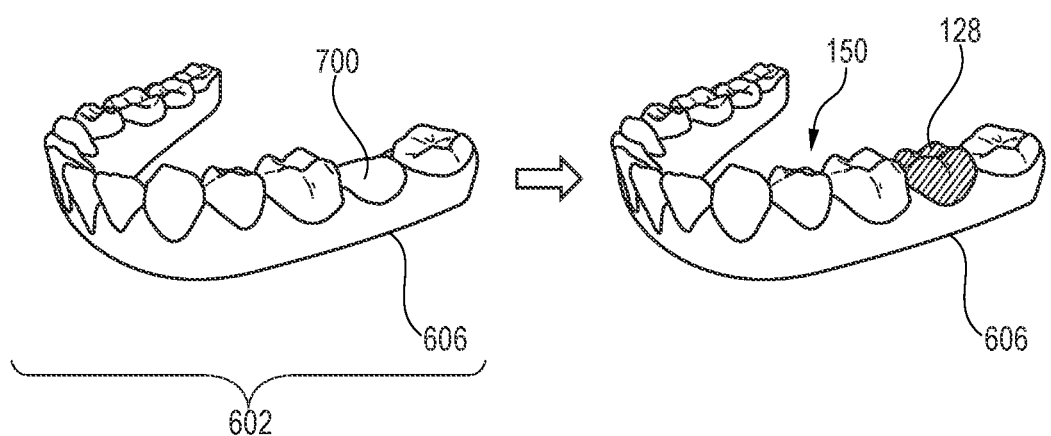
FIG. 7 illustrates an example of a segmentation of a digital dental structure.

FIG. 7 shows a further segmentation 602, but in this case, there is a missing tooth 700. To the right of the segmentation 602 is shown an example of where the generated three-dimensional digital model of the replacement tooth 128 has been used to fill the spot where the missing tooth 700 is.

Figure 8:
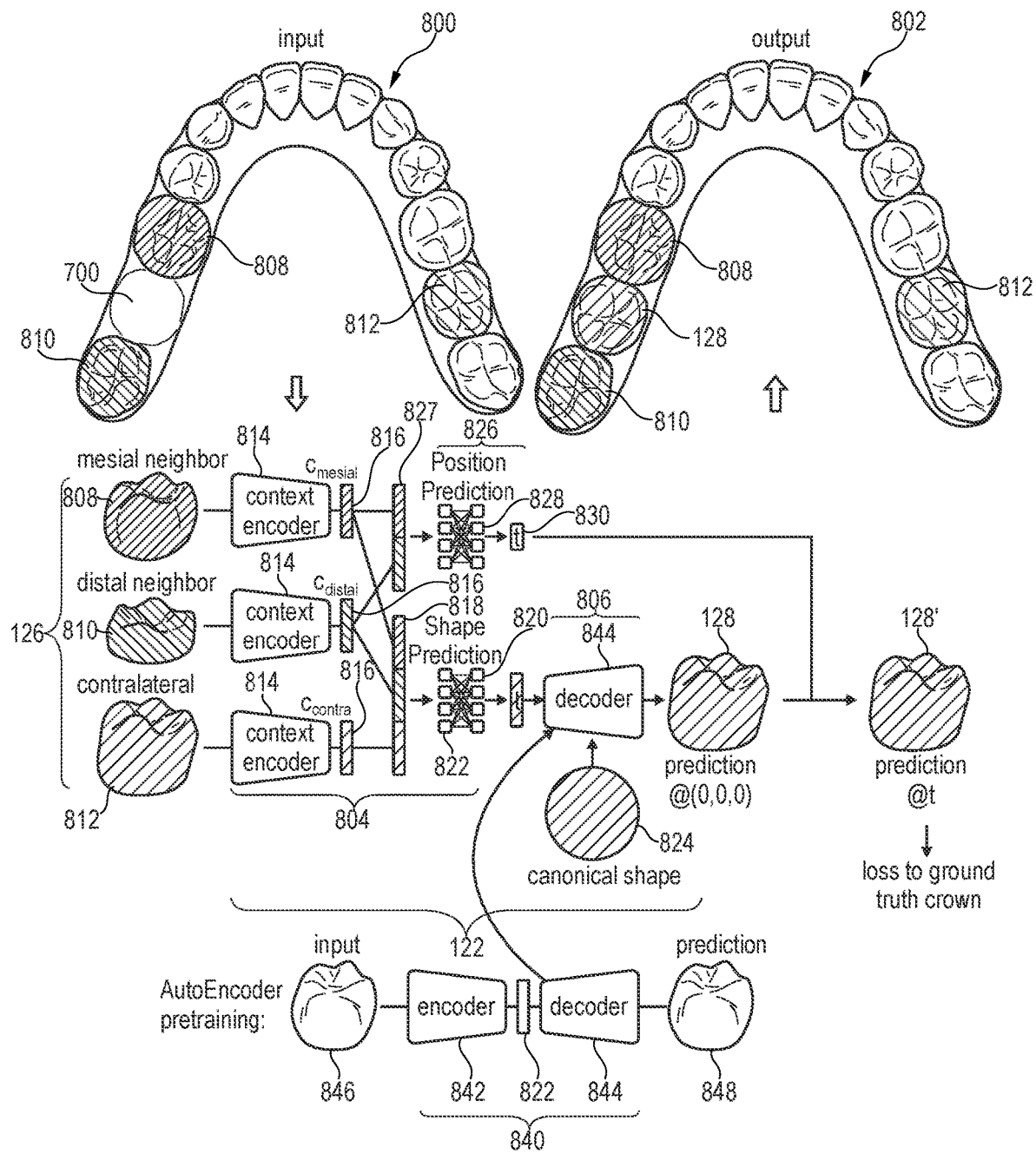
FIG. 8 illustrates a structure of a tooth model generating neural network.

FIG. 8 illustrates the structure and operation of the tooth model generating neural network 122. It is shown as comprising an encoder portion 804 and the decoder portion 806. A number of individual three-dimensional digital tooth models 126 are input into the encoder portion 804. In this case it is a mesial neighbor 808, a distal neighbor 810 and a contralateral tooth 812. Above the diagram of the tooth model generating neural network 122 is an example of the mesh models used for input 800 and for output 802. The teeth 808, 810, and 812 are illustrated as well as the position of a missing tooth 700. The output shows the same except with the generated three-dimensional digital model of the replacement tooth 128 inserted where the missing tooth spot 700 is.

The encoder portion 804 is shown as having a tooth-specific context encoder 814 that receives each of the one or more three-dimensional digital tooth models 126 individually. Each tooth-specific context encoder 814 then outputs a tooth feature vector 816. These are then concatenated into the collective feature vector 818. The collective feature vector 818 then passes through several fully connected layers 820, where it is converted into a latent space vector 822. The latent space vector 822 then controls the decoder portion 806 to output the generated three-dimensional digital model of the replacement tooth 128. In this example, the decoder portion 806 takes a canonical shape 824 and distorts it into the generated three-dimensional digital model of the replacement tooth 128.

The tooth model generating neural network 122 is also shown as optionally containing a position prediction portion 826 that takes an additional feature vector 827 as input into more fully connected layers 828, which then outputs position coordinates 830. These position coordinates 830 can be provided individually or appended to the generated three-dimensional digital model of the replacement tooth 128 to provide a generated three-dimensional digital model of the replacement tooth with positioning coordinates 128'. For example, these coordinates could be simply appended to it or the actual position of the model may be shifted using these coordinates.

Below the diagram of the tooth model generating neural network 122 is a diagram of an autoencoder neural network 840. This is used to illustrate how the decoder portion 806 can be trained in advance of the rest of the tooth model generating neural network 122. The autoencoder neural network 840 comprises an autoencoder encoding portion 842 and an autoencoder decoding portion 844. There is a latent space vector 822 between them. This can be trained by inputting different three-dimensional digital models of a selected tooth as input and then comparing this to an autoencoded three-dimensional digital tooth model 848. A potential benefit to training the decoder portion 806 separately is that the resulting generated three-dimensional digital model of the replacement tooth 128 can be generated more accurately and with less training data. Another benefit is that the autoencoder neural network 840 used during this training may be repurposed to perform style transfer between teeth of the subject and the generated three-dimensional digital model of the replacement tooth. This may result in replacement teeth that looked much more realistic than if a neural network were only used.

Figure 9:
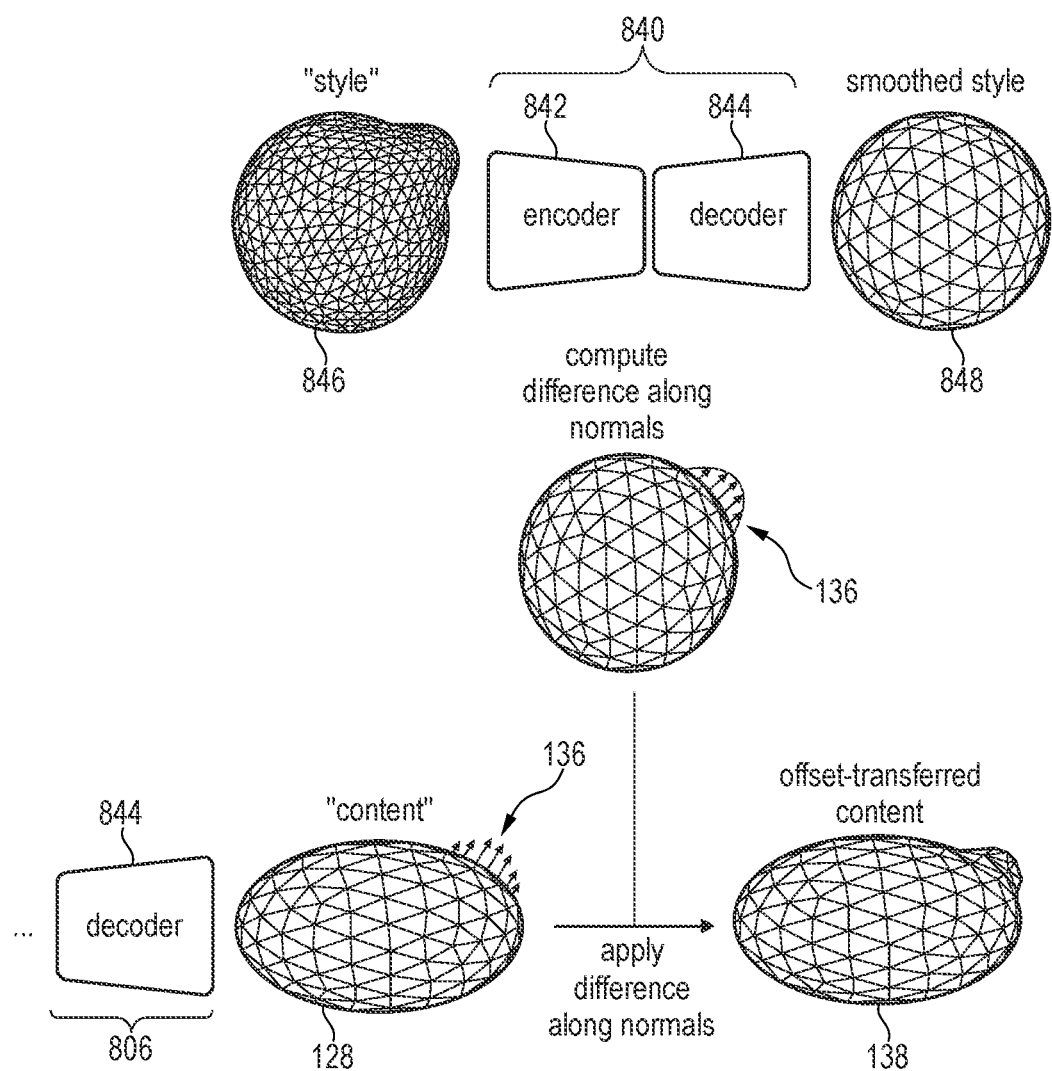
FIG. 9 illustrates a method for a style transfer from a natural tooth to a neural network generated one using an autoencoder.

FIG. 9 illustrates how the autoencoder neural network 840 that was used for training may be used to provide style transfer between an existing tooth of the subject and a tooth generated by a neural network. The autoencoder neural network 840 takes as input the three-dimensional digital model of a selected tooth 846 of the subject. This for example may be a tooth that is measured with an optical scanner. The three-dimensional digital model of the selected tooth 846 shows the detailed structure of the subject's tooth. This is then passed through the autoencoder neural network to result in the autoencoded three-dimensional digital tooth model 848. This tooth is similar; however, it has been artificially smoothed in comparison to the three-dimensional digital model of the selected tooth 846.

A difference between these two models 846, 848 is computed along the normals for the planes defined by the vertices. This results in a series of vectors, which may be used to translate these surfaces. These vectors are one example of a surface modification 136. Below this the generated three-dimensional digital model of the replacement tooth 128 is received from the decoder portion 806 of the tooth model generating neural network 122.

The surface modification 136 is then applied to the same normals to obtain the surface modified generated three-dimensional digital model of the replacement tooth 138. As the decoder portion 806 is identical with the autoencoder decoding portion 844, it smoothes the models in the same way. The surface modification 136 is therefore able to add the same type of surface roughness and structure to make the surface modified generated three-dimensional digital model of the replacement tooth look more realistic.

Figure 10:
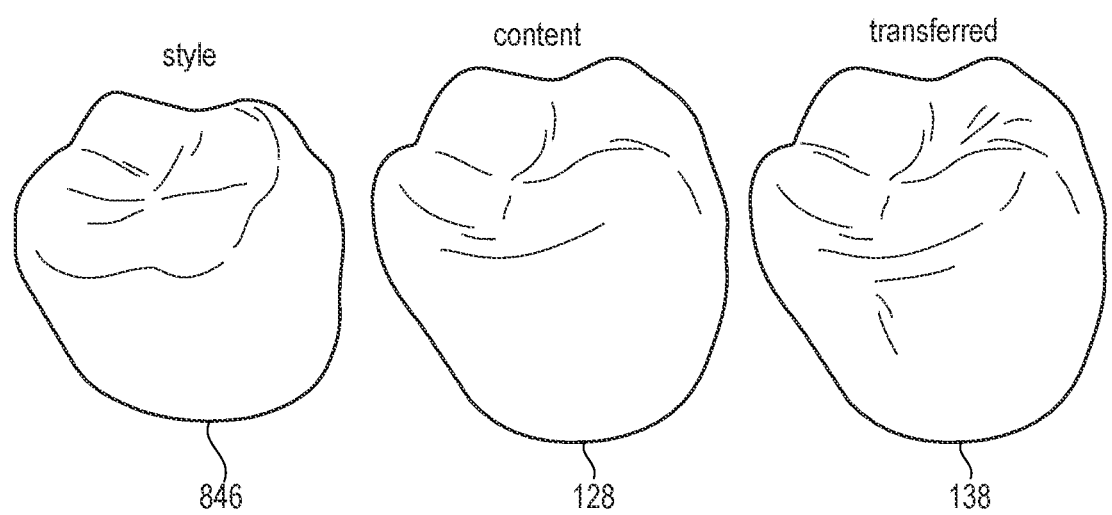
FIG. 10 illustrates the results of the method in FIG. 9.

This is illustrated in FIG. 10. The tooth labeled 128 is the generated three-dimensional digital model of the replacement tooth. The tooth labeled 846 is the three-dimensional digital model of the selected tooth and is a tooth which is selected to provide a style which is then added to the generated three-dimensional digital model of the replacement tooth 128. Tooth labeled 138 is the modified tooth 128 with the style from tooth 846 added to it. It can be seen that the tooth 138 looks much more realistic and more like the style tooth 846. The tooth 128 looks artificially smoothed.

Figure 11:
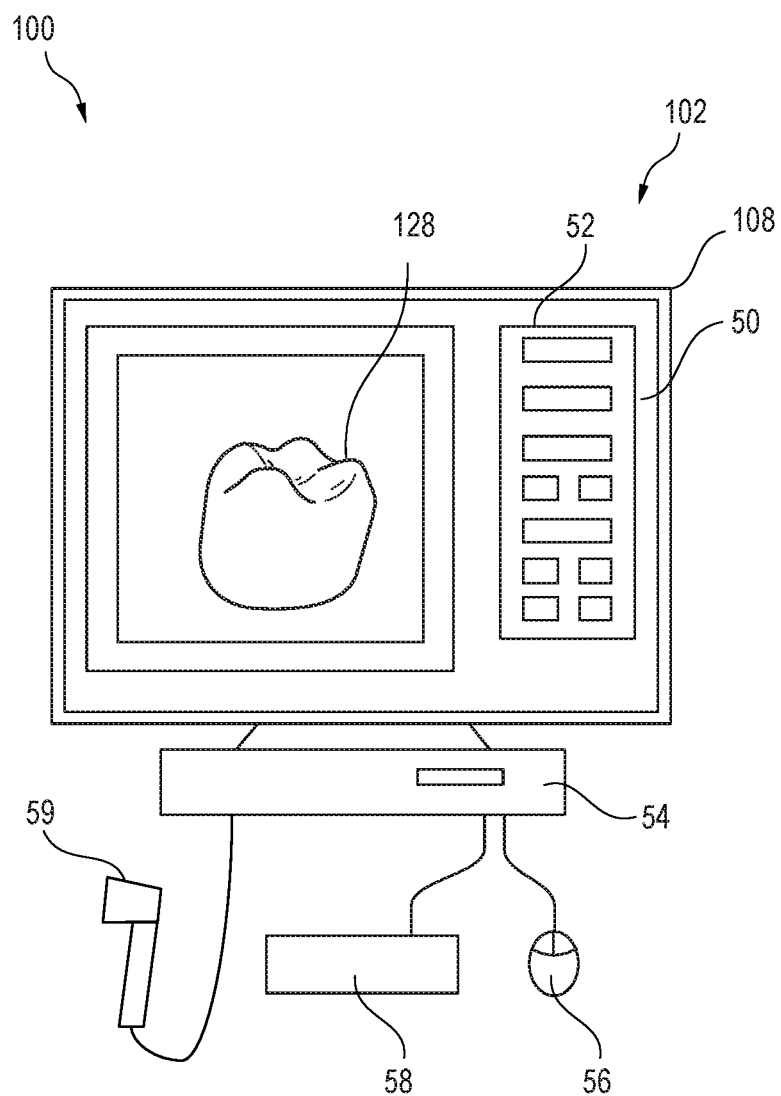
FIG. 11 illustrates a further example of a dental system.

FIG. 11 shows an exemplary dental system 100 with a computer device 102, like the computer device 102 of FIG. 1 or FIG. 3, which is configured to execute one or more of the dental methods according to FIG. 2, FIG. 4 and/or FIG. 5. The computer device 102 may comprise a hardware component 54 comprising one or more processors as well as a memory storing machine-executable program instructions. Execution of the program instructions by the one or more processors may cause the one or more processors to control the computer device 102 to execute one or more of the dental methods according to FIG. 2, FIG. 4 and/or FIG. 5.

The computer device 102 may further comprise one or more input devices, like a keyboard 58 and a mouse 56, enabling a user to interact with the computer device 102. Furthermore, the computer device 102 may be provided with one or more output devices, like a display 108 providing a graphical user interface 50 with control elements 52, e.g., GUI elements, enabling the user to control the execute one or more of the dental methods according to FIG. 2, FIG. 4 and/or FIG. 5. The display 108 is shown to display a generated three-dimensional digital model 128 of the replacement tooth. The computer device 102 may further be provided with a three-dimensional imaging system in form of an optical scanner 59 configured for acquiring a three-dimensional digital dental structure of the subject. This scanner 59 may, e.g., be an intraoral scanner configured to scan a dental structure of the subject within the subject's mouth. This scanner 59 may, e.g., be a scanner configured for scanning an impression of the subject's dental structure, i.e., a negative of the respective dental structure, and/or for scanning used a dental cast, i.e., a positive of the respective dental structure.

Figure 12:
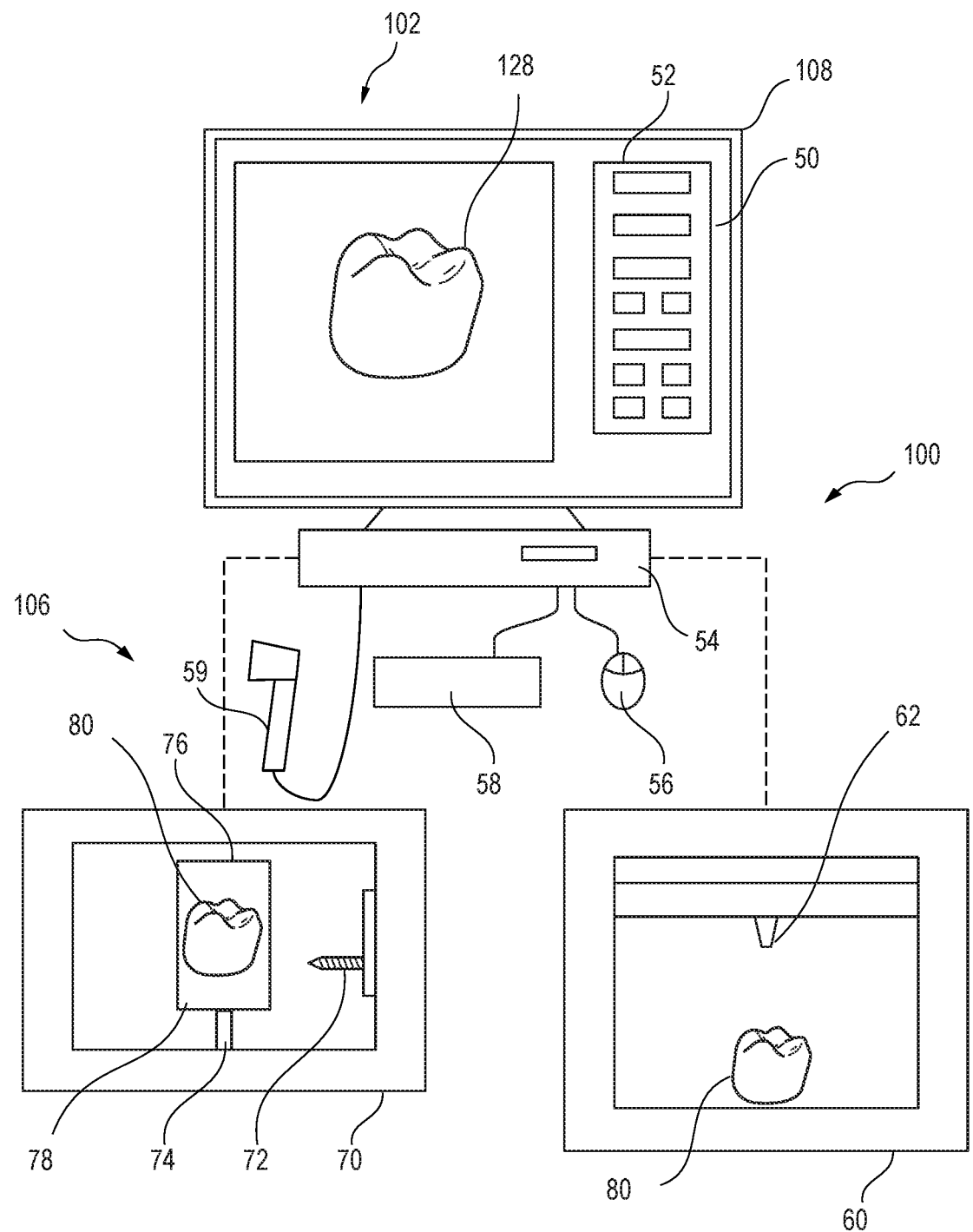
FIG. 12 illustrates a further example of a dental system.

FIG. 12 shows the exemplary dental system 100 of FIG. 11, which further comprises an exemplary fabrication system 106 for fabricating a physical dental restoration model 80 using the generated three-dimensional digital model 128 of the replacement tooth as a template. The dental restoration model 80 being fabricated is a physical copy of at least a part of the respective template 128. The computer device 102 may be configured to control one or more fabrication devices 60, 70. For example, the fabrication system 106 may comprise a fabrication device in form of a machining device 70 controlled by the computer device 102. The machining device 70 may be configured to machining a blank 76 using one or more machining tools 72. The blank 76 of raw material 78, may be provided using a holding device 74 and cut into a desired shape and size of the element to be manufactured, e.g., the dental restoration model 80. The machining tool 72 may, e.g., be a milling tool.

For example, the fabrication system 106 may comprise a fabrication device in form of a three-dimensional printing device 60. The three-dimensional printing device 60 may be controlled by the computer device 102 and configured to print an element to be manufactured, e.g., the dental restoration model 80. The three-dimensional printing device 60 may comprise a printing element 62 configured to print the respective element, like the dental restoration model 80, layer by layer. The printing element 62 may, e.g., comprise a nozzle configured for distributing printing material.

For example, the one or more fabrication devices 60, 70 may be configured for fabricating a casting mold, which is used, e.g., by an additional casting device (not shown) for casting the dental restoration model 80 by injecting casting material into the casting mold. A curing of the casting material may then result in the dental restoration model 80.

Although the invention has been described in reference to specific embodiments, it should be understood that the invention is not limited to these examples only and that many variations of these embodiments may be readily envisioned by the skilled person after having read the present disclosure. The invention may thus further be described without limitation and by way of example only by the following embodiments. The following embodiments may contain preferred embodiments. Accordingly, the term "clause" as used therein may refer to such a "preferred embodiment".

Clause 1. A dental method, wherein the method comprises:
  receiving a selection of a replacement tooth for a subject;
    receiving one or more three-dimensional digital tooth models descriptive of one or more teeth of the subject; and
    receiving a generated three-dimensional digital model of the replacement tooth in response to inputting the one or more three-dimensional digital tooth models descriptive of one or more teeth of the subject into a tooth model generating neural network, wherein the tooth model generating neural network comprises an encoder portion and a decoder portion, wherein the encoder portion is configured for outputting a collective feature vector descriptive of the one or more digital tooth models, wherein the tooth model generating neural network further comprises at least one fully connected layer configured to output a latent space vector in response to receiving the collective feature vector, wherein the decoder portion is configured to output the generated three-dimensional digital model of the replacement tooth in response to receiving the latent space vector.

Clause 2. The dental method of Clause 1, wherein the method further comprises selecting the tooth model generating neural network for generating the replacement tooth from a collection of tooth model generating neural networks trained for a specific tooth or trained for a specific tooth type using the selection of the replacement tooth.

Clause 3. The dental method of Clause 1 or 2, wherein the encoder portion comprises a tooth specific context encoder neural network for each of the one or more three-dimensional digital tooth models, wherein the tooth specific context encoder neural network is configured to output a tooth feature vector in response to receiving a three-dimensional digital tooth model of the one or more three-dimensional digital tooth models, and wherein the tooth model generating neural network is further configured to form the collective feature vector by concatenating the tooth feature vector of at least some of the tooth specific context encoder neural network.

Clause 4. The dental method of Clause 3, wherein the context encoder neural network any one of the following: a surface based encoder, a DiffusionNet encoder, a graph-based encoder, a Graph Neural Network, a point-based encoder, a PointNet encoder, a voxel based encoder, three-dimensional ShapeNet, a three dimensional convolutional neural network, a multi-view rendering based neural network, a two-dimensional convolution neural network, an implicit surface based encoder, an Occupancy Network, and an encoder portion of a convolutional autoencoder.

Clause 5. The dental method of any one of the preceding Clauses, wherein the one or more teeth of the subject comprise any one of the following: one or more adjacent teeth of the replacement tooth, a contralateral tooth of the replacement tooth, a group or partial dental arch, one or more antagonist teeth of the replacement tooth, and combinations thereof.

Clause 6. The dental method of any one of the preceding Clause, wherein the one or more three-dimensional digital tooth models comprise tooth coordinates descriptive of a location within the subject's mouth, wherein the one or more teeth of the subject comprise one or more adjacent teeth of the replacement tooth and/or wherein the one or more teeth of the subject comprise one or more antagonist teeth of the replacement tooth, wherein the tooth generating neural network is further configured to output placement coordinates of the replacement tooth in response to receiving the one or more three-dimensional digital tooth models as input.

Clause 7. The dental method of Clause 6, wherein the tooth model generating neural network is configured to output the placement coordinates of the replacement tooth.

Clause 8. The dental method of Clause 7, wherein the decoder portion is configured for outputting the placement coordinates.

Clause 9. The dental method of Clause 7, wherein the tooth model generating neural network further comprises a position prediction portion configured for outputting the placement coordinates, and wherein the position prediction portion is configured for receiving a concatenation of a tooth feature vector of the one or more adjacent teeth that are descriptive of the tooth coordinates as input.

Clause 10. The dental method of Clause 9, wherein the position prediction portion comprises one or more connected layers.

Clause 11. The dental method of any one of the preceding claims, wherein the decoder portion is implemented as any one of the following: a decoder of an autoencoder, a variational autoencoder decoder portion, an auto decoder, a generative adversarial network, a normalizing flow model, a diffusion model, and autoregressive model.

Clause 12. The dental method of any one of the preceding Clauses, wherein the latent space of the decoder portion is regularized.

Clause 13. The dental method of Clause 12, wherein the method further comprises iteratively modifying the generated three-dimensional digital model of the replacement tooth by modifying the latent space vector using an optimization to minimize a loss function that enforces interproximal contact with one or more adjacent teeth of the replacement tooth.

Clause 14. The dental method of Clause 13, wherein the loss function further enforces any one of the following:
avoiding occlusal contacts of greater than a predefined maximum depth;
enforcing contact with the antagonist tooth of the replacement tooth at predefined landmarks; and
combinations thereof.

Clause 15. The dental method of any one of the preceding Clauses, wherein the method further comprises:
receiving a surface modification; and
applying the surface modification to the generated three-dimensional digital model of the replacement tooth.

Clause 16. The dental method of Clause 15, wherein the surface modification is received from a database of surface modifications.

Clause 17. The dental method of Clause 15, wherein the method further comprises:
receiving an autoencoded three-dimensional digital tooth model in response to inputting a three-dimensional digital model of a selected tooth of the subject into a tooth replicating autoencoder neural network, wherein the tooth replicating autoencoder neural network comprises an autoencoder encoding portion and an autoencoder decoding portion, wherein the autoencoder decoding portion is identical with the decoder portion of the tooth model generating neural network; and
determining the surface modification to morph the autoencoded three-dimensional digital tooth model into the three-dimensional digital model of the selected tooth of the subject.

Clause 18. The dental method of any one of Clauses 15, 16, or 17, wherein the selected tooth is any one of the following: a contralateral tooth of the replacement tooth, an adjacent tooth of the replacement tooth, and an antagonist tooth of the replacement tooth; and wherein the method further comprises applying a mirror image transformation to the surface modification if the selected tooth is the contralateral tooth or the antagonist tooth.

Clause 19. The dental method of any one of the preceding Clauses, wherein the decoder portion is configured output the generated three-dimensional digital model by morphing a canonical shaped mesh into the generated three-dimensional digital model of the replacement tooth.

Clause 20. The dental method of any one of the preceding Clauses, wherein the method further comprises: acquiring a three-dimensional digital dental structure of the subject using a three-dimensional imaging system.

Clause 21. The dental method of Clause 20, wherein the one or more three-dimensional digital tooth models are selected from a segmentation of the three-dimensional digital dental structure using a predetermined criterion.

Clause 22. The dental method of any one of the preceding Clauses, wherein the method further comprises rendering a display of a set of one or more three-dimensional digital tooth models of the subject including the generated three-dimensional digital model of the replacement tooth.

Clause 23. The dental method of any one of the preceding Clauses, wherein the method further comprises fabricating a dental restoration model using the generated three-dimensional digital model of the replacement tooth.

Clause 24. A dental system, wherein the dental system comprises:
a memory storing machine executable instructions and a tooth model generating neural network, wherein the tooth model generating neural network comprises an encoder portion and a decoder portion, wherein the encoder portion is configured for outputting a collective feature vector descriptive of one or more digital tooth models, wherein the tooth model generating neural network further comprises at least one fully connected layer configured to output a latent space vector in response to receiving the collective feature vector, wherein the decoder portion is configured to output a generated three-dimensional digital model of the replacement tooth in response to receiving the latent space vector; and a computational system, wherein execution of the machine executable instructions causes the computational system to:
  receive a selection of a replacement tooth for a subject;
  receive one or more three-dimensional digital tooth models descriptive of one or more teeth of the subject; and
  receive the generated three-dimensional digital model of the replacement tooth in response to inputting the one or more three-dimensional digital tooth models descriptive of one or more teeth of the subject into the tooth model generating neural network.

Clause 25. The dental system of Clause 24, wherein the dental system further comprises a fabrication system configured to fabricate a dental restoration model using the generated three-dimensional digital model of the replacement tooth.

Clause 26. A computer program comprising machine executable instructions and a tooth model generating neural network, wherein the tooth model generating neural network comprises an encoder portion and a decoder portion, wherein the encoder portion is configured for outputting a collective feature vector descriptive of one or more digital tooth models, wherein the tooth model generating neural network further comprises at least one fully connected layer configured to output a latent space vector in response to receiving the collective feature vector, wherein the decoder portion is configured to output a generated three-dimensional digital model of the replacement tooth in response to receiving the latent space vector, wherein execution of the machine executable instructions causes the computational system to:
receive a selection of a replacement tooth for a subject;
receive one or more three-dimensional digital tooth models descriptive of one or more teeth of the subject; and
receive the generated three-dimensional digital model of the replacement tooth in response to inputting the one or more three-dimensional digital tooth models descriptive of one or more teeth of the subject into the tooth model generating neural network.

Clause 27. A dental method, wherein the dental method comprises:
receiving a generated three-dimensional digital model of a replacement tooth of a subject;
receiving a three-dimensional digital model of a selected tooth of the subject;
receiving an autoencoded three-dimensional digital tooth model in response to inputting the three-dimensional digital model of the selected tooth of the subject into an autoencoder neural network, wherein the autoencoder neural network comprises an autoencoder encoding portion and an autoencoder decoding portion;
determining a surface modification to morph the autoencoded three-dimensional digital tooth to the selected tooth of the subject; and
applying the surface modification to the generated three-dimensional digital model of the replacement tooth.

Clause 28. The dental method of Clause 27, wherein the selected tooth is any one of the following: a contralateral tooth of the replacement tooth, an adjacent tooth of the replacement tooth, and an antagonist of the replacement tooth; and wherein the method further comprises applying a mirror image transformation to the surface modification if the selected tooth is the contralateral tooth or an antagonist of the replacement tooth.

Clause 29. The dental method of Clause 27 or 28, wherein the method comprises:
receiving the selection of the replacement tooth for a subject;
receiving one or more three-dimensional digital tooth models descriptive of one or more teeth of the subject;
receiving the generated three-dimensional digital model of the replacement tooth of the subject in response to inputting the one or more three-dimensional digital tooth models into a tooth model generating neural network, wherein the tooth model generating neural network comprises a encoder portion and the decoder portion, wherein the decoder portion is identical with the autoencoder decoding portion, wherein the encoder portion is configured for outputting a collective feature vector descriptive of the one or more teeth of the subject, wherein the generating neural network further comprises at least one fully connected layer configured to output a latent space vector in response to receiving the collective feature vector, wherein the decoder portion is configured to output the three-dimensional digital model in response to receiving the latent space vector.

Clause 30. The dental method of Clause 27 or 28, wherein the generated three-dimensional digital model of a replacement tooth is received from a database of generated three-dimensional digital tooth models.

Clause 31. The dental method of any one of Clauses 27 through 30, wherein the decoder portion is configured to generate the generated three-dimensional digital model of the replacement tooth by morphing a canonical shaped mesh.

Clause 32. The dental method of Clause 31, wherein the canonical mesh comprises vertices, wherein the surface modification is determined by calculating a transformation of the vertices of the three-dimensional digital model of the selected tooth along normals until they intersect the autoencoded three-dimensional digital tooth model.

Clause 33. The dental method of any one of Clauses 27 through 31, wherein the surface modification is determined as a displacement mapping between the three-dimensional digital model of the selected tooth and the autoencoded three-dimensional digital tooth model.

Clause 34. A dental system, wherein the dental system comprises:
a memory storing machine executable instructions; and
a computational system, wherein execution of the machine executable instructions causes the computational system to:
  receive a generated three-dimensional digital model of a replacement tooth of a subject;
  receive a three-dimensional digital model of a selected tooth of the subject;
  receive an autoencoded three-dimensional digital tooth model in response to inputting the three-dimensional digital model of the selected tooth of the subject into an autoencoder neural network, wherein the autoencoder neural network comprises an autoencoder encoding portion and an autoencoder decoding portion;
  determine a surface modification to morph the autoencoded three-dimensional digital tooth to the selected tooth of the subject; and apply the surface modification to the generated three-dimensional digital model of the replacement tooth.

Clause 35. The dental system of Clause 34, wherein the dental system further comprises a fabrication system configured to fabricate a dental restoration model using the generated to three-dimensional digital model of the replacement tooth with the applied surface modification.

Clause 36. A computer program comprising machine executable instructions, wherein execution of the machine executable instructions causes a computational system to:

receive a generated three-dimensional digital model of a replacement tooth of a subject;

receive a three-dimensional digital model of a selected tooth of the subject; receiving an autoencoded three-dimensional digital tooth model in response to inputting the three-dimensional digital model of the selected tooth of the subject into an autoencoder neural network, wherein the autoencoder neural network comprises an autoencoder encoding portion and an autoencoder decoding portion;

determine a surface modification to morph the autoencoded three-dimensional digital tooth to the selected tooth of the subject; and apply the surface modification to the generated three-dimensional digital model of the replacement tooth.

Clause 37. A dental method, wherein the method comprises:

receiving a generated three-dimensional digital model of a replacement tooth of a subject, wherein the generated three-dimensional digital model is formed from a mesh with a mesh topology comprising vertices;

receiving a surface modification to be transferred to the mesh forming the generated three-dimensional digital model, the surface modification being defined for the same mesh topology as the mesh forming the generated three-dimensional digital model and comprising a location adjustment for the vertices of the mesh topology; and applying the surface modification to the mesh forming the generated three-dimensional digital model of the replacement tooth.

Clause 38. The dental method of Clause 37, wherein the surface modification is received from a database of surface modifications.

Clause 39. The dental method of Clause 37, wherein the method further comprises: receiving an autoencoded three-dimensional digital tooth model in response to inputting a three-dimensional digital model of a selected tooth of the subject into a tooth replicating autoencoder neural network, wherein the tooth replicating autoencoder neural network comprises an autoencoder encoding portion and an autoencoder decoding portion, wherein the autoencoder decoding portion is identical with the decoder portion of the tooth model generating neural network; and determining the surface modification to morph the autoencoded three-dimensional digital tooth model into the three-dimensional digital model of the selected tooth of the subject.

Clause 40. The dental method of any one of Clauses 37, 38, or 39, wherein the selected tooth is any one of the following: a contralateral tooth of the replacement tooth, an adjacent tooth of the replacement tooth, and an antagonist tooth of the replacement tooth; and wherein the method further comprises applying a mirror image transformation to the surface modification if the selected tooth is the contralateral tooth or the antagonist tooth.

Clause 41. A dental system, wherein the dental system comprises:

a memory storing machine executable instructions; and a computational system, wherein execution of the machine executable instructions causes the computational system to:

receive a generated three-dimensional digital model of a replacement tooth of a subject, wherein the generated three-dimensional digital model is formed from a mesh with a mesh topology comprising vertices;

receive a surface modification to be transferred to the mesh forming the generated three-dimensional digital model, the surface modification being defined for the same mesh topology as the mesh forming the generated three-dimensional digital model and comprising a location adjustment for the vertices of the mesh topology; and apply the surface modification to the mesh forming the generated three-dimensional digital model of the replacement tooth.

Clause 42. The dental system of Clause 41, wherein the dental system further comprises a fabrication system configured to fabricate a dental restoration model using the generated three-dimensional digital model of the replacement tooth.

Clause 43. Computer program comprising machine executable instructions, wherein execution of the machine executable instructions causes a computational system to: receive a generated three-dimensional digital model of a replacement tooth of a subject, wherein the generated three-dimensional digital model is formed from a mesh with a mesh topology comprising vertices;

receive a surface modification to be transferred to the mesh forming the generated three-dimensional digital model, the surface modification being defined for the same mesh topology as the mesh forming the generated three-dimensional digital model and comprising a location adjustment for the vertices of the mesh topology; and apply the surface modification to the mesh forming the generated three-dimensional digital model of the replacement tooth.

LIST OF REFERENCE NUMERALS 50 user interface
52 control elements
54 hardware device
56 keyboard
58 mouse
59 scanner
60 3D printing device
62 printing element
70 machining device
72 machining tool
74 holding device
76 blank
78 raw material
80 physical dental restoration model
100 dental system
102 computer
104 digital model source 106 fabrication system
108 display
110 computational system
112 hardware interface
114 user interface
116 memory
120 machine executable instructions
122 tooth model generating neural network
124 selection of a replacement tooth
126 one or more three-dimensional digital tooth models
128 generated three-dimensional digital model of the replacement tooth
128' generated three-dimensional digital model of the replacement tooth with position coordinates
130 collection of tooth model generating neural networks
132 placement coordinates of generated three-dimensional digital model of the replacement tooth
134 optimization algorithm
136 surface modification
138 surface modified generated three-dimensional digital model of the replacement tooth
140 computer added design module
142 control commands
150 set of one or more three-dimensional digital tooth models
300 dental system
302 three-dimensional digital model of a selected tooth
304 autoencoder neural network
306 autoencoded three-dimensional digital tooth model
136 surface modification
138 surface modified generated three-dimensional digital model of the replacement tooth
200 receive a selection of a replacement tooth for a subject
202 receive one or more three-dimensional digital tooth models descriptive of one or more teeth of the subject
204 select the tooth model generating neural network for generating the replacement tooth from a collection of tooth model generating neural networks trained for a specific tooth or trained for a specific tooth type using the selection of the replacement tooth
206 receive a generated three-dimensional digital model of the replacement tooth in response to inputting the one or more three-dimensional digital tooth models descriptive of one or more teeth of the subject into a tooth model generating neural network
208 iteratively modify the generated three-dimensional digital model of the replacement tooth by modifying the latent space vector using an optimization to minimize a loss function.
210 output placement coordinates of the replacement tooth
212 receive a surface modification
214 apply the surface modification
216 render a display of a set of one or more three-dimensional digital tooth models of the subject including the generated three-dimensional digital model of the replacement tooth
218 fabricate a dental restoration using the generated three-dimensional digital model of the replacement tooth
308 library of three-dimensional digital tooth models
310 database of surface modifications
400 receive a generated three-dimensional digital model of a replacement tooth
402 receive a three-dimensional digital model of a selected tooth
404 receive an autoencoded three-dimensional digital tooth model in response to inputting the three-dimensional digital model of the selected tooth into an autoencoder neural network
406 determine a surface modification to morph the autoencoded three-dimensional digital tooth to three-dimensional digital model of the selected tooth
600 three-dimensional digital dental structure
602 segmentation
604 three-dimensional digital tooth models
606 gingiva
700 missing tooth
800 input meshes
802 output meshes
804 encoder portion
806 decoder portion
808 mesial neighbor
810 distal neighbor
812 contralateral
814 tooth specific contex encoder
816 tooth feature vector
818 collective feature vector
820 fully connected layers
822 latent space vector
824 canonical shape
826 position prediction portion
827 additional feature vector
828 fully connected layers
830 position coordinates
840 autoencoder neural network
842 autoencoder encoding portion
844 autoencoder decoding portion
846 three-dimensional digital model of a selected tooth
848 autoencoded three-dimensional digital tooth model

What is claimed is:

1. A dental method, wherein the method comprises:
receiving a selection of a replacement tooth for a subject;
receiving one or more three-dimensional digital tooth models descriptive of one or more teeth of the subject different from the replacement tooth; and
receiving a generated three-dimensional digital model of the replacement tooth in response to inputting the one or more three-dimensional digital tooth models descriptive of one or more teeth of the subject into a tooth model generating neural network, wherein the tooth model generating neural network comprises an encoder portion and a decoder portion, wherein the encoder portion is configured for outputting a collective feature vector descriptive of the one or more digital tooth models, wherein the tooth model generating neural network further comprises at least one fully connected layer configured to output a latent space vector in response to receiving the collective feature vector, wherein the decoder portion is configured to output the generated three-dimensional digital model of the replacement tooth in response to receiving the latent space vector.

2. The dental method of claim 1, wherein the method further comprises selecting the tooth model generating neural network for generating the replacement tooth from a collection of tooth model generating neural networks trained for a specific tooth or trained for a specific tooth type using the selection of the replacement tooth.

3. The dental method of claim 1, wherein the encoder portion comprises a tooth specific context encoder neural network for each of the one or more three-dimensional digital tooth models, wherein the tooth specific context encoder neural network is configured to output a tooth feature vector in response to receiving a three-dimensional digital tooth model of the one or more three-dimensional digital tooth models, and wherein the tooth model generating neural network is further configured to form the collective feature vector by concatenating the tooth feature vector of at least some of the tooth specific context encoder neural network.

4. The dental method of claim 3, wherein the context encoder neural network is any one of the following: a surface based encoder, a DiffusionNet encoder, a graph-based encoder, a Graph Neural Network, a point-based encoder, a PointNet encoder, a voxel based encoder, three-dimensional ShapeNet, a three dimensional convolutional neural network, a multi-view rendering based neural network, a two-dimensional convolution neural network, an implicit surface based encoder, an Occupancy Network, and an encoder portion of a convolutional autoencoder.

5. The dental method of claim 1, wherein the one or more teeth of the subject comprise any one of the following: one or more adjacent teeth of the replacement tooth, a contralateral tooth of the replacement tooth, a group or partial dental arch, one or more antagonist teeth of the replacement tooth, and combinations thereof.

6. The dental method of claim 1, wherein the one or more three-dimensional digital tooth models comprise tooth coordinates descriptive of a location within the subject's mouth, wherein the one or more teeth of the subject comprise one or more adjacent teeth of the replacement tooth and/or wherein the one or more teeth of the subject comprise one or more antagonist teeth of the replacement tooth, wherein the tooth generating neural network is further configured to output placement coordinates of the replacement tooth in response to receiving the one or more three-dimensional digital tooth models as input.

7. The dental method of claim 6, wherein the tooth model generating neural network is configured to output the placement coordinates of the replacement tooth.

8. The dental method of claim 7, wherein the decoder portion is configured for outputting the placement coordinates.

9. The dental method of claim 7, wherein the tooth model generating neural network further comprises a position prediction portion configured for outputting the placement coordinates, and wherein the position prediction portion is configured for receiving a concatenation of a tooth feature vector of the one or more adjacent teeth that are descriptive of the tooth coordinates as input.

10. The dental method of claim 9, wherein the position prediction portion comprises one or more connected layers.

11. The dental method of claim 1, wherein the decoder portion is implemented as any one of the following: a decoder of an autoencoder, a variational autoencoder decoder portion, an auto decoder, a generative adversarial network, a normalizing flow model, a diffusion model, and autoregressive model.

12. The dental method of claim 1, wherein the latent space of the decoder portion is regularized.

13. The dental method of claim 12, wherein the method further comprises iteratively modifying the generated three-dimensional digital model of the replacement tooth by modifying the latent space vector using an optimization to minimize a loss function that enforces interproximal contact with one or more adjacent teeth of the replacement tooth.

14. The dental method of claim 13, wherein the loss function further enforces any one of the following:

avoiding occlusal contacts of greater than a predefined maximum depth;
enforcing contact with an antagonist tooth of the replacement tooth at predefined landmarks; and
combinations thereof.

15. The dental method of claim 1, wherein the method further comprises:
receiving a surface modification; and
applying the surface modification to the generated three-dimensional digital model of the replacement tooth.

16. The dental method of claim 15, wherein the surface modification is received from a database of surface modifications.

17. The dental method of claim 15, wherein the method further comprises: receiving an autoencoded three-dimensional digital tooth model in response to inputting a three-dimensional digital model of a selected tooth of the subject into a tooth replicating autoencoder neural network, wherein the tooth replicating autoencoder neural network comprises an autoencoder encoding portion and an autoencoder decoding portion, wherein the autoencoder decoding portion is identical with the decoder portion of the tooth model generating neural network; and
determining the surface modification to morph the autoencoded three-dimensional digital tooth model into the three-dimensional digital model of the selected tooth of the subject.

18. The dental method of claim 15, wherein the selected tooth is any one of the following: a contralateral tooth of the replacement tooth, an adjacent tooth of the replacement tooth, and an antagonist tooth of the replacement tooth; and wherein the method further comprises applying a mirror image transformation to the surface modification if the selected tooth is the contralateral tooth or the antagonist tooth.

19. The dental method of claim 1, wherein the decoder portion is configured output the generated three-dimensional digital model by morphing a canonical shaped mesh into the generated three-dimensional digital model of the replacement tooth.

20. The dental method of claim 1, wherein the method further comprises: acquiring a three-dimensional digital dental structure of the subject using a three-dimensional imaging system.

21. The dental method of claim 20, wherein the one or more three-dimensional digital tooth models are selected from a segmentation of the three-dimensional digital dental structure using a predetermined criterion.

22. The dental method of claim 1, wherein the method further comprises rendering a display of a set of one or more three-dimensional digital tooth models of the subject including the generated three-dimensional digital model of the replacement tooth.

23. The dental method of claim 1, wherein the method further comprises fabricating a dental restoration model using the generated three-dimensional digital model of the replacement tooth.

24. A dental system, wherein the dental system comprises:
a memory storing machine executable instructions and a tooth model generating neural network, wherein the tooth model generating neural network comprises an encoder portion and a decoder portion, wherein the encoder portion is configured for outputting a collective feature vector descriptive of one or more digital tooth models, wherein the tooth model generating neural network further comprises at least one fully connected layer configured to output a latent space vector in response to receiving the collective feature vector, wherein the decoder portion is configured to output a generated three-dimensional digital model of a replacement tooth in response to receiving the latent space vector; and a computational system, wherein execution of the machine executable instructions causes the computational system to:

receive a selection of the replacement tooth for a subject;

receive one or more three-dimensional digital tooth models descriptive of one or more teeth of the subject different from the replacement tooth;

receive the generated three-dimensional digital model of the replacement tooth in response to inputting the one or more three-dimensional digital tooth models descriptive of one or more teeth of the subject into the tooth model generating neural network.

25. The dental system of claim 24, wherein the dental system further comprises a fabrication system configured to fabricate a dental restoration model using the generated three-dimensional digital model of the replacement tooth.

26. A computer program product comprising a non-transitory computer readable storage medium comprising machine executable instructions and a tooth model generating neural network, wherein the tooth model generating neural network comprises an encoder portion and a decoder portion, wherein the encoder portion is configured for outputting a collective feature vector descriptive of one or more digital tooth models, wherein the tooth model generating neural network further comprises at least one fully connected layer configured to output a latent space vector in response to receiving the collective feature vector, wherein the decoder portion is configured to output a generated three-dimensional digital model of a replacement tooth in response to receiving the latent space vector, wherein execution of the machine executable instructions causes a computational system to:

receive a selection of the replacement tooth for a subject;

receive one or more three-dimensional digital tooth models descriptive of one or more teeth of the subject different from the replacement tooth; and receive the generated three-dimensional digital model of the replacement tooth in response to inputting the one or more three-dimensional digital tooth models descriptive of one or more teeth of the subject into the tooth model generating neural network.

* * * * *